(12) United States Patent
Suen et al.

(10) Patent No.: US 9,962,427 B2
(45) Date of Patent: May 8, 2018

(54) TREATMENT OF RIGHT VENTRICULAR DYSFUNCTION DUE TO PRESSURE OVERLOAD

(71) Applicant: OTTAWA HOSPITAL RESEARCH INSTITUTE, Ottawa (CA)

(72) Inventors: Colin Suen, Ottawa (CA); Lynn Megeney, Ottawa (CA); Duncan J. Stewart, Ottawa (CA); Mohammad Abdul-Ghani, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 0 days. days.

(21) Appl. No.: 15/206,889

(22) Filed: Jul. 11, 2016

(65) Prior Publication Data

US 2018/0008673 A1 Jan. 11, 2018

(51) Int. Cl.
*A61P 9/04* (2006.01)
*A61K 38/19* (2006.01)
*A61K 38/20* (2006.01)
*C07K 14/52* (2006.01)
*C07K 14/54* (2006.01)

(52) U.S. Cl.
CPC .............. *A61K 38/19* (2013.01); *A61K 38/20* (2013.01); *A61K 38/204* (2013.01); *C07K 14/52* (2013.01); *C07K 14/54* (2013.01); *C07K 14/5412* (2013.01)

(58) Field of Classification Search
None
See application file for complete search history.

(56) References Cited

U.S. PATENT DOCUMENTS

| 5,571,893 A | 11/1996 | Baker et al. |
| 2006/0115464 A1 | 6/2006 | Megeney |

FOREIGN PATENT DOCUMENTS

| WO | 9730146 A2 | 8/1997 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Nomura et al, 2003. Ann Thorac Surg. 237-243.*
Suen et al, Oct. 2015. Canadian Journal of Cardiology. 31(10): S142-S143.*
Mohammed et al (2014. Circulation 130:2310-2320).*
Bhuiyan et al., "Heart Failure with Preserved Ejection Fraction: Persistent Diagnosis, Therapeutic Enigma," Current Cardiovascular Risk Reports, Oct. 2011, vol. 5 (5), pp. 440-449.
Bogaard et al., "The Right Ventricle Under Pressure, Cellular and Molecular Mechanisms of Right-Heart Failure in Pulmonary Hypertension," CHEST Recent Advances in Chest Medicine, Mar. 2009, vol. 135 (3), pp. 794-804.
Cuspidi et al., "Prevalence and Clinical Correlates of Right Ventricular Hypertrophy in Essential Hypertension," Journal of Hypertension, Apr. 2009, vol. 27 (4), pp. 854-860.
Guazzi., "Pulmonary Hypertension in Heart Failure Preserved Ejection Fraction," Circulation Heart Failure, Mar. 2014, vol. 7, pp. 367-377.
Jiang et al., "Core 5. Myocardium: Function and Failure, Session Title: Vascular Disease and Pulmonary Hypertension, Abstract 12273: High Mortality in the Fischer Rat Model of Severe Pulmonary Arterial Hypertension Linked to Strain-Specific Deficiency in Right Ventricular Adaptation," Circulation, Nov. 25, 2014, vol. 130, Issue Supp 2, 2 pages.
Jin et al., "In Vivo Effects of Cardiotrophin-1," Cytokine, Dec. 1996, vol. 8 (12), pp. 920-926.
Kevin et al., "Right Ventricular Failure," Continuing Education in Anaesthesia, May 2007, vol. 7 (3), pp. 89-94.
Scharhag et al., "Althete's Heart, Right and Left Ventricular Mass and Function in Male Endurance Athletes and Untrained Individuals Determined by Magnetic Resonance Imaging" Journal of the American College of Cardiology, Nov. 2002, vol. 40 (10), pp. 1856-1863.
Simon et al., "Right Ventricular Dysfunction and Failure in Chronic Pressure Overload," Cardiology Research and Practice, Mar. 2011, vol. 2011, 7 pages.
Voelkel et al., "Right Ventricular Function and Failure, Report of a National Heart, Lung, and Blood Institute Working Group on Cellular and Molecular Mechanisms of Right Heart Failure," Circulation, Oct. 2006, vol. 114 (17), pp. 1883-1891.
Vonk-Noordegraaf et al., "Right Heart Adaptation to Pulmonary Arterial Hypertension," Journal of American College of Cardiology, Dec. 2013, vol. 62 (25), pp. D22-D33.

* cited by examiner

*Primary Examiner* — Zachary Howard
(74) *Attorney, Agent, or Firm* — Borden Ladner Gervais LLP

(57) ABSTRACT

A method is disclosed for inducing right ventricular (RV) adaptive remodeling in a patient suffering from pulmonary hypertension (PH) due to pressure overload comprising administering a therapeutically effective amount of a carditrophin-1 polypeptide, recombinant protein or a polynucleotide encoding CT-1 polypeptide or full-length protein.

10 Claims, 9 Drawing Sheets

FIG. 1A
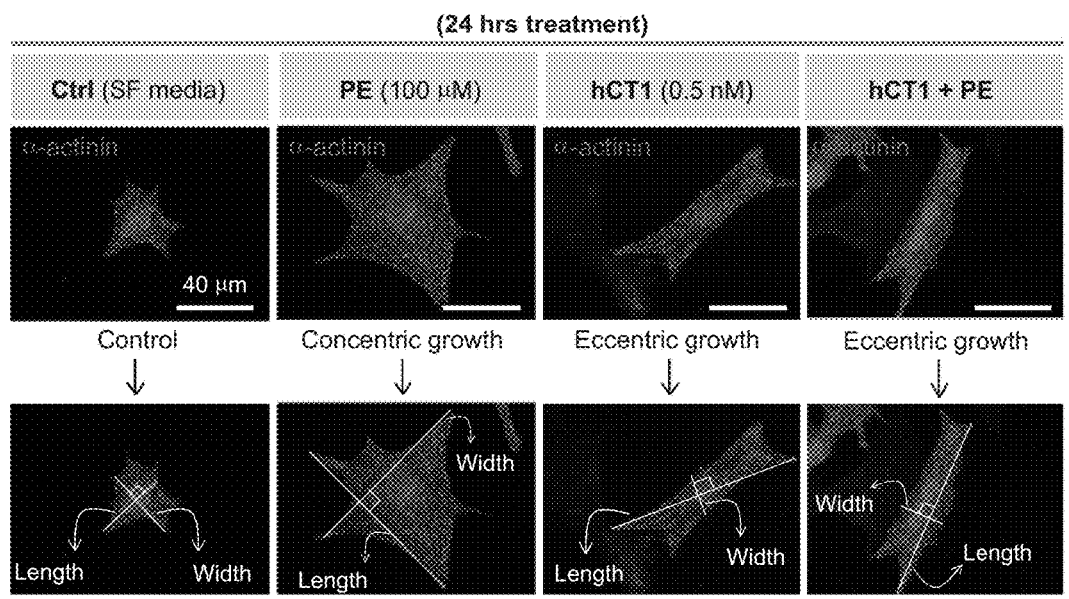
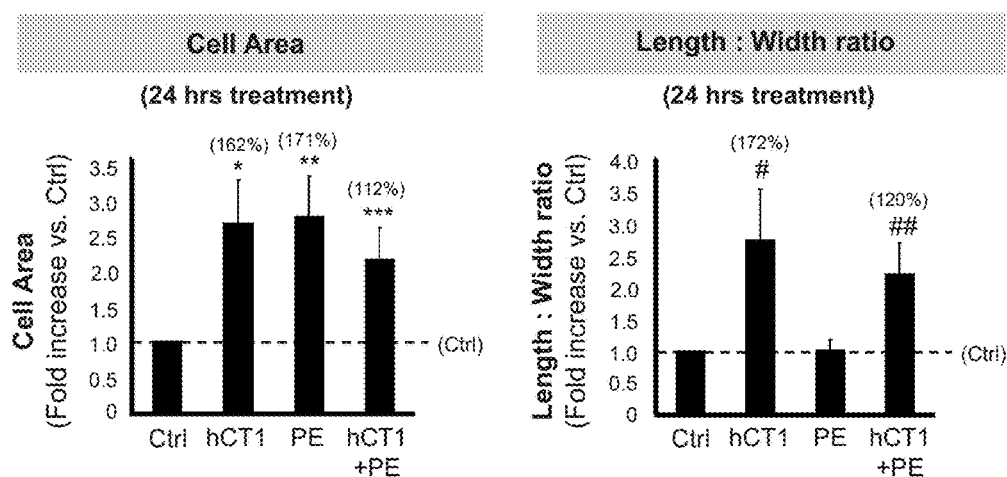
FIG. 1B

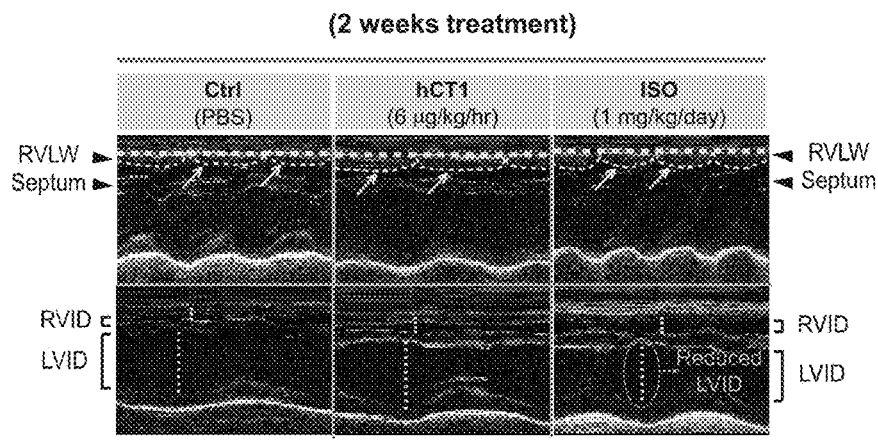
FIG. 3A
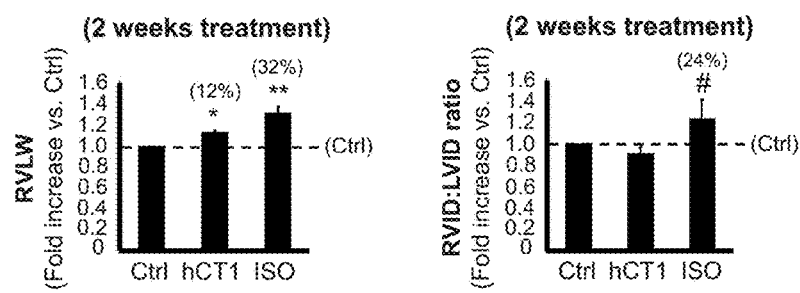
FIG. 3B
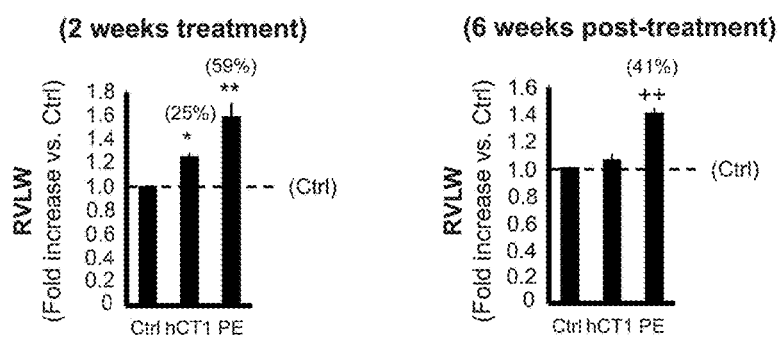
FIG. 3C
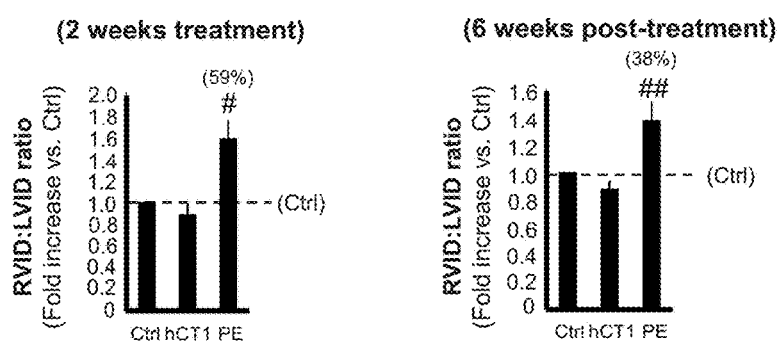

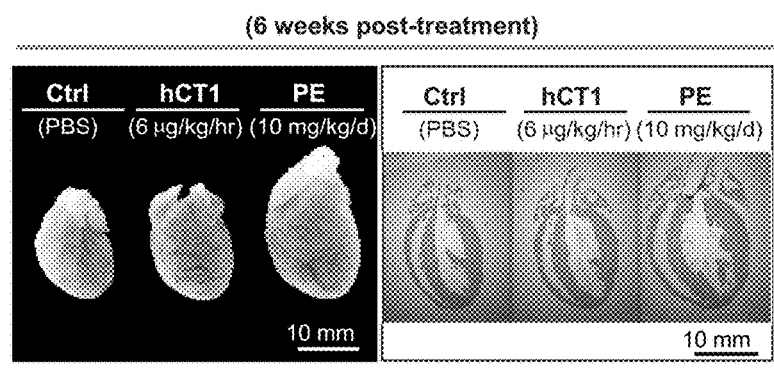
FIG. 4A
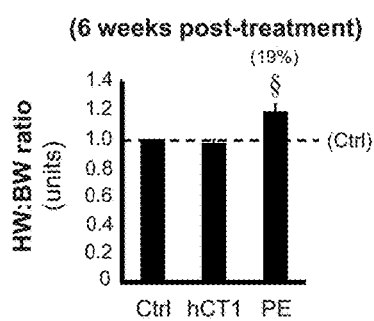
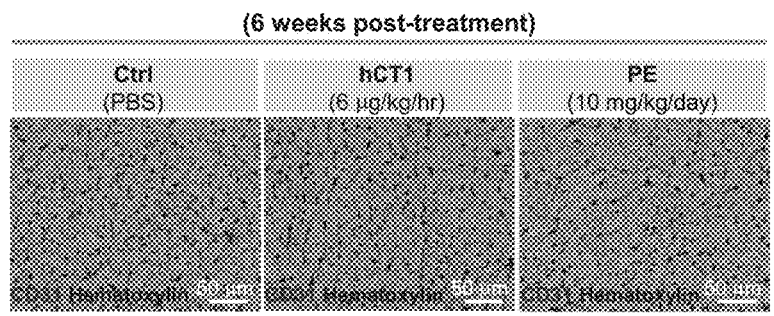
FIG. 4B
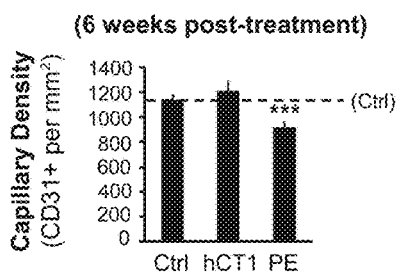

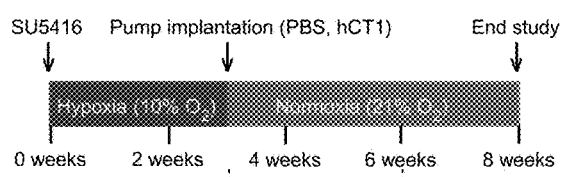
FIG. 5A
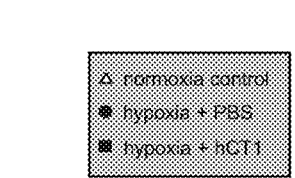
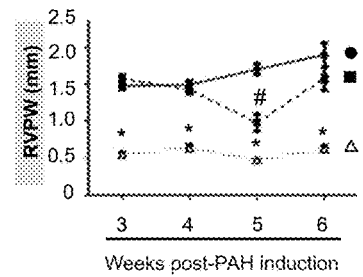
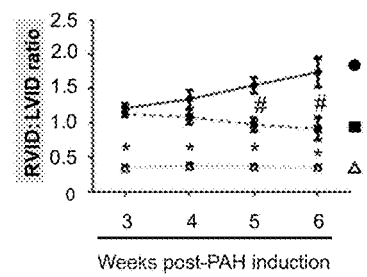
FIG. 5B
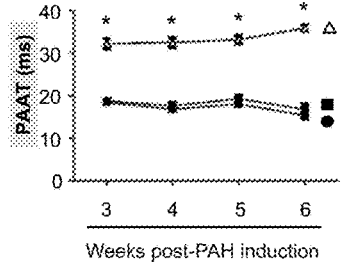
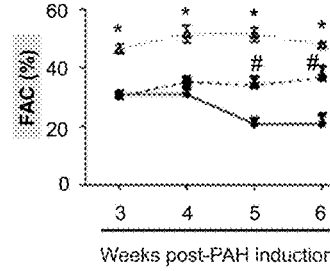
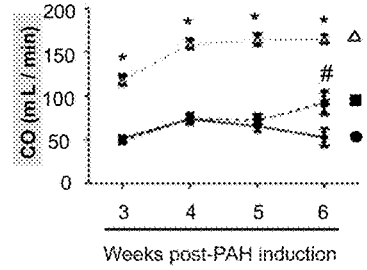

FIG. 6A
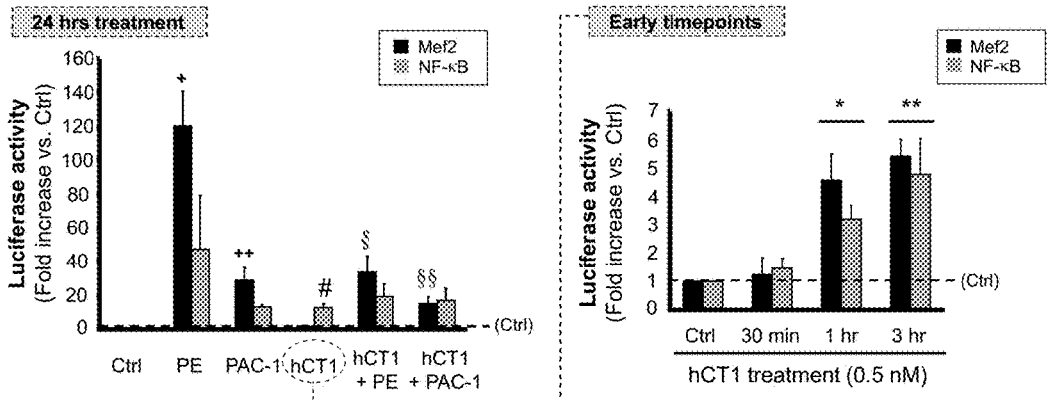
FIG. 6B
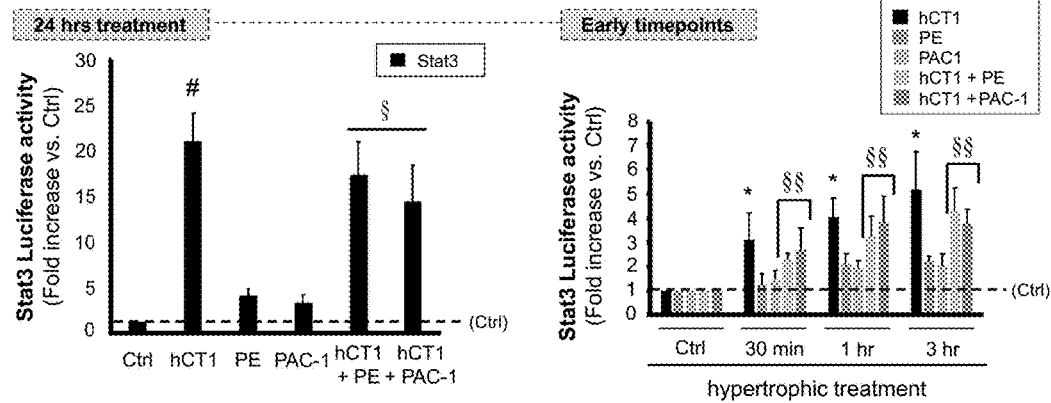
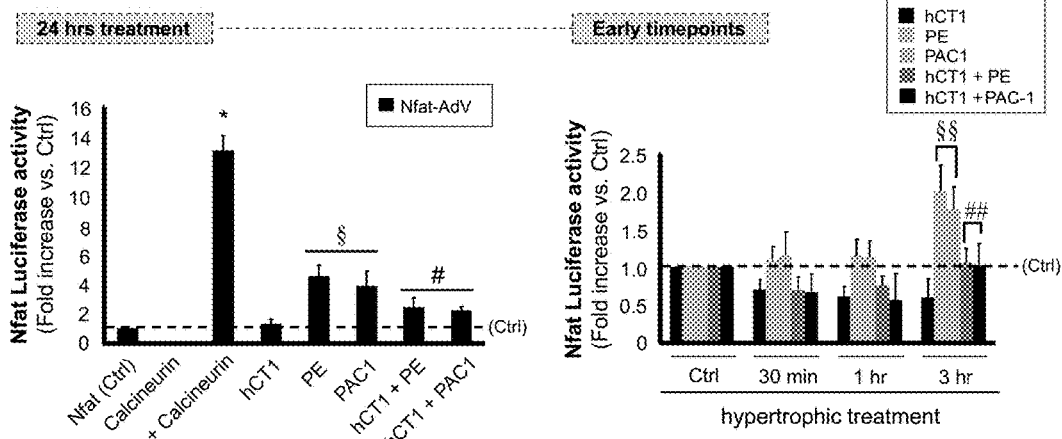
FIG. 6C

FIG. 7A
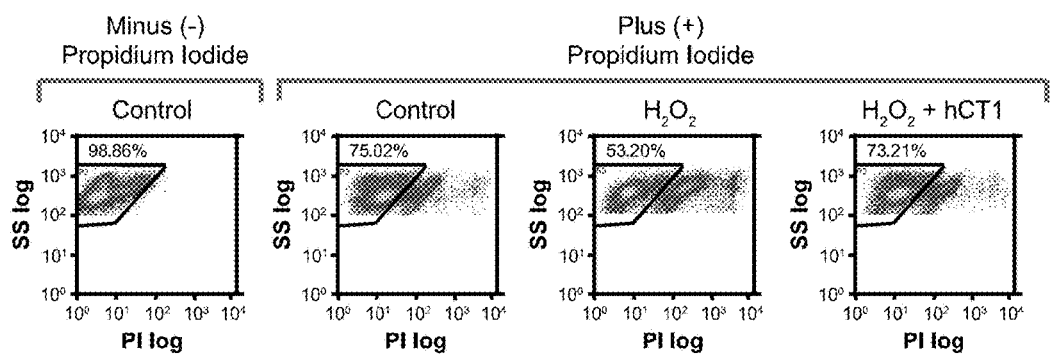
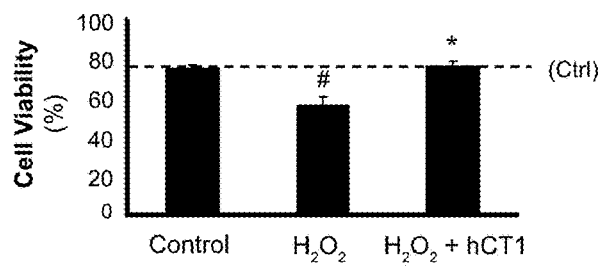
FIG. 7B
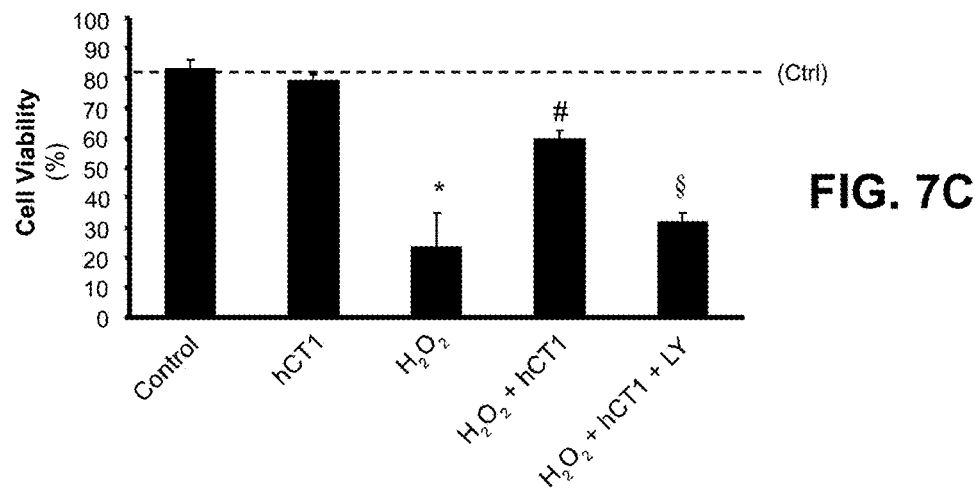
FIG. 7C

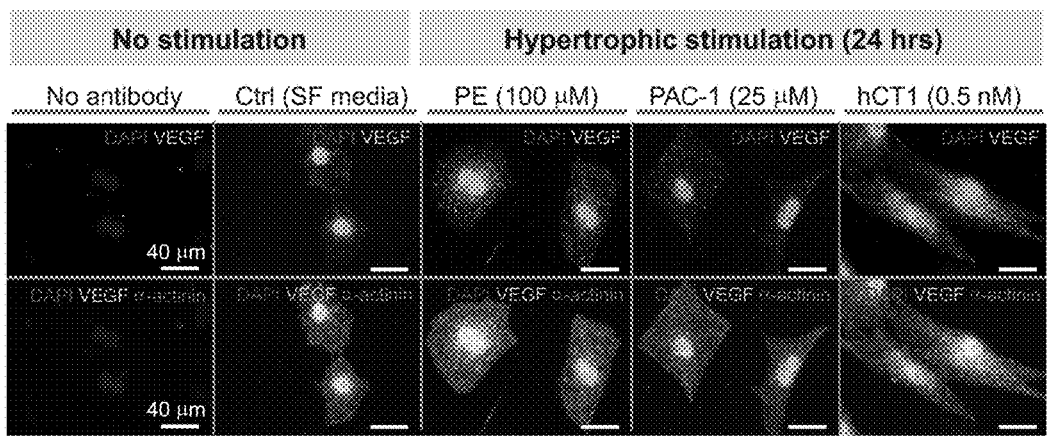

| | Gene name | Gene symbol | Accession # | Fold change (vs. Ctrl) |
|---|---|---|---|---|
| Angiogenesis & Endothelial Growth/Survival Factors | Angiopoietin-like 4 | Angptl4 | NM_199115 | 2.62 |
| | Fms-related tyrosine kinase 4 | Flt4 | NM_053652 | 2.26 |
| | Von Willebrand factor 5A | Vwa5a | NM_198755 | 2.03 |
| | Vascular Endothelial Growth Factor A | Vegfa | NM_031836 | 1.14 |
| Antimicrobial Peptides | Regenerating islet-derived 3 gamma | Reg3g | NM_173097 | 28.39 |
| | Regenerating islet-derived 1 alpha | Reg1a | NM_012641 | 7.96 |
| | Regenerating islet-derived 3 beta | Reg3b | NM_053289 | 6.14 |
| | Hepcidin Antimicrobial Peptide | Hamp | NM_053469 | 2.70 |
| Pro-survival Receptors | Phosphoinositide-3-kinase, subunit 1, alpha | Pik3r1 | NM_013005 | 1.56 |
| | Phosphoinositide-3-kinase, subunit 6 | Pik3r6 | NM_001081444 | 1.49 |

TREATMENT OF RIGHT VENTRICULAR DYSFUNCTION DUE TO PRESSURE OVERLOAD

FIELD OF THE INVENTION

The present disclosure relates to methods, compositions, and uses of such compositions for treating right ventricular dysfunction due to pressure overload.

BACKGROUND OF THE INVENTION

Heart failure occurs when the heart is unable to pump sufficient blood to meet the body's needs. Until relatively recently, research and treatment has focused on left ventricular failure (or left heart failure). In fact, generally the term heart failure has been used when referring to left ventricle dysfunction and/or congestive heart failure. More recently the importance of the right ventricle in heart failure has been recognized; however treatments for right ventricular dysfunction are lacking.

The right ventricle (RV) is structurally different from the left ventricle (LV). For instance, the left ventricle is more muscular, being responsible for receiving oxygenated blood from the left atrium and pumping it through the aorta at relatively high pressures into the systemic circulation, supplying blood to all organs and tissues of the body. In contrast, the right ventricle receives deoxygenated venous blood from all organs and tissues of the body through the right atrium, and pumps the blood, representing the entire cardiac output, to a single organ—the lungs—at remarkably low pressures. In addition, the RV is derived from a different set of precursor cells, has a more complex 3D morphological shape, usually operates at much lower pressures (afterload), and has a distinct contraction pattern. Given the different structure of the right ventricle and that it operates under different hemodynamic conditions, it is not surprising that the RV responds differently to loading conditions, like chronically elevated pressure (afterload). Pressure overload refers to the pathological state of cardiac muscle resulting from having to contract while experiencing an excessive afterload (pressure). The most common causes of RV pressure overload are pulmonary valve stenosis and pulmonary hypertension (PH) from any cause.

Pulmonary hypertension (PH) is characterized by increases in pulmonary arterial pressure and therefore RV systolic pressure (RVSP), and has been classified into 5 groups (the WHO classification) as follows:
  Group 1, pulmonary arterial hypertension (PAH);
  Group 2, PH due to left heart disease and elevated LV filling (venous) pressures;
  Group 3, PH due to lung diseases and/or hypoxia;
  Group 4, chronic thromboembolic PH; and
  Group 5, PH with unclear multifactorial mechanisms.

Cardiac ventricular remodeling refers to changes in size, shape, structure, and physiology of the main pumping chambers of the heart. In response to increased ventricular afterload (myocardial wall tension during systole), individual cardiomyocytes increase in size (i.e. myocyte hypertrophy), the myocardium thickens (myocardial hypertrophy) to normalize ventricular wall tension (therefore afterload), thereby eliminating the initial stress and maintaining normal cardiac output to meet the systemic demands of the body. One aspect of ventricular remodeling, namely ventricular hypertrophy, relates to the thickening of the ventricular walls (pumping chambers) in the heart. These remodeling responses can be either physiological (adaptive/beneficial/compensatory) or pathological (maladaptive/harmful/adverse/noncompensatory) and are associated with distinct structural changes in heart (at the gross morphologic and cellular level), and differences at the molecular level in gene expression and signal transduction pathways.

Pathological (or maladaptive) cardiac remodeling is a progressive form of organ growth, whereby initial contractile improvements are rapidly curtailed by unrestrained enlargement of the myocardium proper. New sarcomeres are added in-parallel with existing sarcomeres (i.e. the cardiomyocytes thicken rather than lengthen) in response to chronic pressure overload. This type of remodeling is also termed concentric remodeling. Thus, the cardiac wall thickens and the chamber volume is initially maintained or reduced. However, the right ventricle cannot sustain long term pressure overload, and RV pathological cardiac remodeling is eventually characterized by an increase in the size of the RV chamber (RV dilation) and reduced contractile function.

Adaptive compensation or physiological cardiac remodeling is a beneficial form of myocardial growth, arising from a compensatory response to conditions that require increased blood volumes such as pregnancy and chronic aerobic exercise training. Dissimilar to pathologic remodeling, physiologic growth of the myocardium is characterized by enhanced cardiac function and modest increases in ventricle dimensions. If the precipitating stress is volume overload (as through aerobic exercise, which increases venous return to the heart through the action of the skeletal-muscle pump), the cardiac muscle responds by adding new sarcomeres in-series with existing sarcomeres (i.e. the cardiomyocytes lengthen more than thicken). This type of growth is also termed eccentric hypertrophy. An essential hallmark of physiologic hypertrophy that distinguishes this form of growth from pathologic hypertrophy is the reversibility of the cell growth, whereby the removal of the stimulus leads to a complete reversion of the adaptation.

Functional limitations and prognosis in PH (regardless of the Group) is determined largely by the degree to which the RV can adapt to increased RV pressure and afterload. If the RV can remodel in a compensatory manner and maintain its systolic function, then even severe PH can be well tolerated. However, if the RV is unable to adapt to increasing afterload, it will undergo noncompensatory remodeling characterized eventually by an increase in the size of the RV chamber (RV dilation) and reduced contractile function. In other words, a decrease in RV function will lead to a lack of oxygen perfusion as the pumping of blood to the lungs with its concurrent oxygenation will decrease (among other problems). This leads to clinical symptoms and signs of right heart failure (RVF or RHF), with progressive limitation in the ability of the right heart to accommodate increases in cardiac output (CO) during exercise (shortness of breath on exertion, SOBOE) and ultimately even at rest (NYHA class IV heart failure). Deteriorating RV function and dropping CO can also lead to a drop in the systemic arterial blood pressure during exercise that results in presyncope and syncope (fainting), a characteristic symptom of advanced PH, and ultimately death. In other words, a progressive right heart failure develops owing to the sustained RV pressure overload. The disease course has been characterized as consisting of an early, "compensated" stage associated with right heart physiological remodeling but normal RV diameter and function, followed by transition to a decompensated state (pathological remodeling) characterized by increasing RV dilatation and worsening contractile function. Therefore, survival of patients with PH is closely related to RV function. In fact RV failure is the cause of at least 70% of deaths attributable to PH.

Despite its importance, until recently the right heart has not received the same degree of research interest as other aspects of PH, and relatively little is known about the mechanisms of right ventricular failure in PH, or the prognostic implications of specific changes in right ventricular structure and function. Pathological right ventricular remodeling has significant prognostic and therapeutic implications to patients with PH. Unfortunately, the pharmacological therapies developed over the last 30 years for the treatment of left heart failure (e.g. congestive heart failure), are not effective in the treatment of RV failure. PAH therapies primarily target the pulmonary vascular abnormalities (primarily vasoconstriction and arterial remodeling), and none of these were designed to directly benefit the right ventricle (RV). In fact, medications for PAH that affect the pulmonary vasculature, may be detrimental to the right heart. Because a patient's functional state and prognosis are largely determined by performance of the RV, there is a need for a treatment for PH which improves the ability of the right ventricle to adapt to increased afterload. Thus, novel therapeutic approaches are urgently needed.

CT-1 expression has recently been associated with an array of cardiac pathologies including: hypertension, myocardial infarction, and heart failure (Jin et al. 1996 Cytokine 10:19-25, Calabro P. et al. 2009 J Mol Cell Cardiol. 46(2): 142-8, Schillaci G. et al. 2013 J Hypertens 31 474-76, Lopez B. et al. 2014 Hypertension 63:483-89). Although these disease studies linked CT-1 to a pathologic outcome, the observations were associations rather than true cause and effect experimentation. Indeed, while some studies associate circulating CT-1 levels with cardiac pathologies, other studies could not confirm these findings (Zile M R et al. 2011 Circ Heart Fail 4:246-56).

SUMMARY OF THE INVENTION

It is an object of the present disclosure to obviate or mitigate at least one disadvantage of previously attempted treatments.

In a first aspect, the present invention provides a method for treating a patient with right ventricular dysfunction due to pressure overload, by inducing right ventricular (RV) adaptive compensation in a patient, comprising administration of a therapeutically effective amount of a cardiotrophin-1 (CT-1) polypeptide or a polynucleotide encoding CT-1 polypeptide, to the patient to treat right heart failure (RVF). In one aspect the patient suffering from right ventricular dysfunction due to pressure overload is suffering from pulmonary hypertension (PH), such as pulmonary arterial hypertension (PAH) or heart failure with preserved ejection fraction (HFpEF).

In one aspect, adaptive compensation may be characterized by reversible eccentric hypertrophy. In one aspect, adaptive compensation may be characterized by an increased RVLW (right ventricle lateral wall) thickness but constant or reduced RVID:LVID (right to left ventricle internal diameters) ratio; this may be relative to a healthy or untreated patient. In one aspect, adaptive compensation may be characterized by the maintenance of efficient contractile function or improved contractile function (e.g. more forceful contraction); this maintenance or improvement may be relative to an untreated patient and/or a patient suffering from pathological remodeling. In one aspect, adaptive compensation may be characterized by increased vascularity. In one aspect, such characteristics are in comparison to pre-treatment values.

In one aspect, the CT-1 polypeptide is a recombinant CT-1 polypeptide.

In one aspect, the invention provides a method for promoting RV adaptive compensation in a patient with right ventricular dysfunction due to pressure overload comprising administration of a therapeutically effective amount of a cardiotrophin-1 (CT-1) polypeptide or a polynucleotide encoding CT-1 polypeptide, to the patient to treat right heart failure (RVF).

In one aspect, the invention provides a method for reversing RV maladaptive compensation in a patient with right ventricular dysfunction due to pressure overload comprising administration of a therapeutically effective amount of a cardiotrophin-1 (CT-1) polypeptide or a polynucleotide encoding CT-1 polypeptide, to the patient to treat right heart failure (RVF).

In another aspect, the invention provides a cardiotrophin-1 (CT-1) polypeptide or a polynucleotide encoding CT-1 polypeptide or compositions comprising as much, for use in the treatment of right ventricular dysfunction due to pressure overload by inducing right ventricular (RV) adaptive compensation in a patient to prevent, delay, or treat right heart failure (RVF) in said patient.

In one aspect, the treatment of RVF is by preventing RVF.
In one aspect, the treatment of RVF is by delaying RVF.
In one aspect, the treatment of RVF is by relieving, reducing or alleviating RVF.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIGS. 1A and 1B. Morphometric analysis of primary cardiomyocytes stimulated with human Cardiotrophin-1 (hCT1) and/or the hypertrophy agonist Phenylephrine (PE). FIG. 1A shows morphology of treated cardiomyocytes by immunofluorescence and FIG. 1B shows quantifications of cell area and length:width ratio of treated cardiomyocytes.

FIG. 2A shows cell morphology by alpha actinin immunofluorescence and quantification of the cell area FIG. 2B shows distribution of cell proportion for length:width ratios.

FIGS. 3A, 3B, and 3C. Echocardiography (ECHO) analysis reveals a state of beneficial/physiologic cardiac adaptive compensation after 2 weeks of hCT1 administration in vivo while reversion to baseline cardiac dimensions is displayed in vivo 6 weeks upon hCT1 withdrawal. FIG. 3A shows M-mode ECHO analysis of the myocardium treated with hCT1 or ISO, a hypertrophy agonist. Arrows (in upper panels) point to myocardial wall (RVLW). Dotted lines (in lower panels) show inner ventricle chambers. FIG. 3B shows quantification of M-mode ECHO analysis for the right ventricle lateral wall thickness (RVLW) and ratio of the right to left ventricle internal diameters (RVID/LVID) of the heart following 2 weeks of treatment with hCT1 or ISO. FIG. 3C shows quantification of M-mode ECHO analysis for the right ventricle lateral wall thickness (RVLW) and ratio of the right to left ventricle internal diameters (RVID/LVID) of hearts treated with hCT1 or PE 2 and 6 weeks after treatment.

FIGS. 4A and 4B. Beneficial/physiologic cardiac adaptive compensation and reversion to baseline cardiac dimensions is observed upon 2 weeks of hCT1 administration in vivo followed by hCT1 withdrawal for 4 weeks. Identical follow-on procedure and analysis as conducted in FIG. 3 above. FIG. 4A Whole hearts and Hematoxylin & Eosin (H & E) stained sections and quantification of the heart weight to body weight (HW:BW) ratio 6 weeks post-treatment with hCT1 or PE. FIG. 4B shows staining and quantification of capillary density by staining for the endothelial cell-specific marker (CD31) and counterstaining for nuclei with Hematoxylin.

FIGS. 5A and 5B. Human Cardiotrophin-1 (hCT1) improves RV adaptation to severe Pulmonary Hypertension (PH) in Fischer rats. FIG. 5A shows the experimental design of this study FIG. 5B shows echocardiography analysis conducted weekly for hCT1 or mock treated rats in which pulmonary hypertension was induced for the following parameters: Right Ventricle Lateral Wall thickness (RVLW), Ratio of Right Ventricle Internal Diameter to Left Ventricle Internal (RVID/LVID), Pulmonary Artery Acceleration Time (PAAT), Fractional Area Change (FAC), and Cardiac Output (CO).

FIGS. 6A, 6B, and 6C. Stimulation with hCT1 causes sustained activation of NF-κB and Stat3 with limited activation of Mef2, as well as limited Nfat activation; the latter two indices are distinct expression patterns from pathologic hypertrophic stimulation. FIG. 6A Primary neonatal cardiomyocytes were transfected with luciferase reporter plasmids (NF-κB or Mef2), as indicators of hypertrophic activity. Luciferase activity was measured after treatments for 24 hrs with: hCT1 (0.5 nM), PE (100 µM), or procaspase 3 activating compound 1, PAC-1 (25 µM) (left). Treatments at early timepoints (30 min, 1 hr, and 3 hr) were also conducted for hCT1 (right). FIG. 6B Primary neonatal cardiomyocytes were transfected with a luciferase reporter plasmid for Stat3. Luciferase activity was measured after treatments for 24 hrs with: hCT1 (0.5 nM), PE (100 µM), or procaspase 3 activating compound 1, PAC-1 (25 µM) (left) and at earlier time points (right). FIG. 6C Primary neonatal cardiomyocytes were infected with a luciferase-based Nfat reporter Adenovirus (Nfat-AdV). Luciferase activity was measured after treatments for 24 hrs with: hCT1 (0.5 nM), PE (100 µM), or procaspase 3 activating compound 1, PAC-1 (25 µM) (left) and at earlier time points (right)

FIGS. 7A 7B and 7C. hCT1 promotes cardioprotection against cytotoxic hydrogen peroxide ($H_2O_2$) stimulation and is PI3K-dependent. FIG. 7A shows side scatter (SS) versus Propidium Iodide (PI) plot for cell viability FACS analysis following a 1 hour treatment of cardiomyocytes with $H_2O_2$ in the presence or absence of hCT1. FIG. 7B Quantitation of cell viability analysis as shown in (A). FIG. 7C Quantification of PI cell viability FACS analysis following a 24 hrs treatment of cardiomyocytes with $H_2O_2$ in the presence or absence of hCT1. Pre-treatment with PI3K inhibitor (LY294002, 50 µM) before $H_2O_2$ was also tested.

FIGS. 8A and 8B. Increased VEGF expression and angiogenesis during cardiac adaptive compensation stimulation with hCT1 compared to pathologic hypertrophic stimulation FIG. 8A shows Vascular Endothelial Growth Factor—VEGF expression by immunofluorescence in primary cardiomyocytes incubated with control serum-free media (Ctrl, SF media) or stimulated with hCT1 (0.5 nM), PE (100 µM), or PAC-1 (25 µM) for 24 hours. FIG. 8B Microarray analysis of primary cardiomyocytes stimulated with hCT1 (0.5 nM) for 24 hours.

FIG. 9A Schematic for cardiac differentiation of pluripotent P19 cells. FIG. 9B Immunofluorescence results for the cardiac-specific marker Troponin T (cTnT) in P19 cardiac cells at day 7 of differentiation in the presence of varying doses of hCT1 ranging from 0-500 ng/mL (0-25 nM). Quantification of expression of cTnT is shown on the graph. FIG. 9C Quantification of beating clusters in P19 cardiac cells at day 13-15 of differentiation in the presence of varying doses of hCT1. FIG. 9D Immunoblot for the cardiac markers cTnT and GATA4 in whole cell lysates from a P19 cardiac differentiation timecourse in the presence and absence of hCT1.

DETAILED DESCRIPTION OF THE INVENTION

Figure 2A:
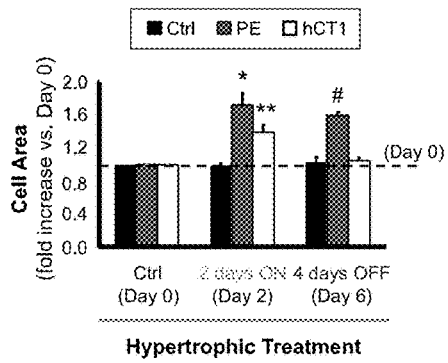
FIGS. 2A and 2B. hCT1 induces physiologic adaptive compensation in vitro with reversion to a normal cardiomyocyte phenotype upon removal of hCT1 stimulation.

RV adaptation and ventricular remodeling in right ventricular dysfunction due to pressure overload is a complex process that depends not only on the severity of pulmonary vascular disease but also on the interplay between neurohormonal activation, coronary perfusion, and myocardial metabolism. A progressive right heart failure develops owing to the sustained RV pressure overload. The disease course has been characterized as consisting of an early, "compensated" stage associated with right heart physiological remodeling, followed by transition to a decompensated state (pathological remodeling) characterized by increasing RV dilatation and worsening contractile function.

The Applicant has found that CT-1 promotes RV adaptive compensation and can reverse maladaptive remodeling. Thus, in patients who have RV dysfunction due to pressure overload and possibly have already developed RVF, CT-1 reverses the maladaptive remodeling by promoting adaptive remodeling and allows the RV to compensate for the increased pressure in afterload.

Applicant's observations demonstrate that cardiomyocytes treated with recombinant human CT1 protein (hCT1) engage a physiologic growth response, adding sarcomeres in series, a cellular/molecular change that is fully reversible with the removal of hCT1. hCT1 administration also overrides concurrent signals that propel pathologic/maladaptive remodeling (such as isoproterenol/phenylephrine). In addition, the Applicant has noted that in vivo delivery of recombinant hCT1 leads to a rapid (14 days) alteration in the structure of the heart, with volume and wall dimension increases characteristic of exercise adaptation, which is a fully reversible response following cessation of hCT1 delivery. Applicants also demonstrated that hCT1 administration can improve cardiac contractile performance in a model of progressive right heart failure (pulmonary hypertension), demonstrating the clinical utility of this protein in an otherwise intractable cardiac disease state for which no known treatment exists.

In one aspect, the present invention provides compositions for use in treating right ventricular dysfunction in the context of PH and/or increased RV afterload due to any cause, in particular by stimulating adaptive right ventricular remodeling.

Possible advantages of the invention may include induction of beneficial physiologic hypertrophy, improved contractile performance of diseased myocardium/heart muscle, improved contractile performance of normal myocardium/heart muscle, improved contractile performance in aged myocardium/heart muscle, improved vascularity angiogenesis in the diseased myocardium/heart muscle, and limitation of fibrosis/scarring in the heart. Other possible advantages include the increased capacity of the RV to cope with or compensate for increased afterload, as well as the delay in RV failure.

PH is increasingly seen as a contributing factor in heart failure (HF) with preserved ejection fraction (HFpEF), now the most common form of HF (Bhatia R S, Tu J V, Lee D S, et al. The New England journal of medicine 2006; 355(3): 260-9; Owan T E, Hodge D O, Herges R M, Jacobsen S J, Roger V L, Redfield M M. The New England journal of medicine 2006; 355(3): 251-9.), in which the symptoms, functional capacity and prognosis are closely linked to the development of PH and right heart failure. At present, there are no effective treatments for HFpEF, apart from general supportive care and fluid management (i.e. diuretics). Therefore, this represents a large and growing patient population that could benefit from a specific therapy to improve RV adaptation while decreasing the negative outcomes associated with prolonged afterload. Other forms of PH such as Group 3 PH due to chronic lung disease and Group 4 PH (i.e. chronic thromboembolic pulmonary hypertension or CTEPH) could also benefit from such an RV targeted therapy.

Definitions

Prior to setting forth the invention in detail, definitions of certain terms to be used herein are provided. Unless defined otherwise, all technical and scientific terms used herein have the same meaning as is commonly understood by one of skill in the art.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "subject" is intended to include animals which are capable of suffering from or afflicted with right ventricular dysfunction due to pressure overload, including due to pulmonary hypertension. Examples of subjects include mammals, e.g., humans, non-human primates, dogs, cows, horses, pigs, sheep, goats, cats, mice, rabbits, and rats. In certain embodiments, the subject is a human, e.g., a human suffering from, at risk of suffering from, or potentially capable of suffering from right ventricular dysfunction due to pressure overload.

The term "treat" is used herein to mean to relieve, reduce or alleviate at least one symptom of a disease in a subject. The term "treat" also encompasses delaying or preventing onset prior to clinical manifestation of a disease or symptom of a disease and/or reducing the risk of developing or worsening of a symptom of a disease.

A "therapeutically effective amount" of a therapeutic agent, or combinations thereof, is an amount sufficient to treat disease in a subject.

The term "about" or "approximately" usually means within 5%, or more preferably within 1%, of a given value or range.

The term "cardiotrophin-1" (CT-1) refers to a mammalian CT-1 (also known as cardiac hypertrophy factor, or CHF). CT-1 is a secreted cytokine that is a member of the larger Interleukin 6 related cytokine family. A number of cardiotrophin proteins are known in the art, for example, but not limited to mouse CT-1 (Pennica, D., et al., Proc. Natl. Acad. Sci. USA, 92:1142-1146) and human CT-1 (Pennica, D., et al., (1996). Cytokine, 8:183-189). CT-1 may be provided as a polypeptide (including the full-length protein), as a recombinant polypeptide (including as a recombinant protein) or as a polynucleotide encoding, and capable of expressing, the polypeptide or full-length protein. The sequences of various CT-1 proteins are known in the art and can be used as a basis for the preparation of CT-1 polypeptides (for example, those provided by the above references and GenBank Accession Nos. AAC52173 and NP031821 (mouse); and AAD12173 and AAA85229 (human)). In one aspect, CT-1 refers to recombinant human CT-1 (recombinant hCT-1).

The term "pulmonary hypertension" (PH) is defined as an elevation in pulmonary arterial pressure (PAP), with the mean PAP>25 mm Hg and systolic PAP>35 mm Hg. Group 1 PH (PAH) is diagnosed if the pulmonary capillary wedge pressure, left atrial pressure, or left ventricular end-diastolic pressure (left heart filling pressure) is mm Hg (V. V. McLaughlin, S. L. Archer, D. B. Badesch et al., Journal of the American College of Cardiology, vol. 53, no. 17, pp. 1573-1619, 2009). Group 2 PH is diagnosed in the context of PAP>25 mm Hg in which left heart filling pressure is ≤15 mm Hg.

"Afterload": Afterload is defined as ventricular wall tension during systole. More commonly, afterload is described as the resistance, impedance, or pressure that the ventricles must overcome to eject their blood volumes. Afterload is dependent on a number of factors, including volume and mass of blood ejected, the size and wall thickness of the ventricles, and the impedance of the vasculature. In the clinical setting, the most sensitive measure of afterload is systemic vascular resistance (SVR) for the left ventricle and pulmonary vascular pressure (PVR) or right ventricular systolic pressure (RVSP) for the right ventricle. Afterload has an inverse relationship to ventricular function. As resistance to ejection increases, the force of contraction decreases, resulting in a decreased stroke volume. As resistance to ejection increases, an increase in myocardial oxygen consumption occurs (Kuhn and Werdan in Holzheimer R G, Mannick J A, editors. Surgical Treatment: Evidence-Based and Problem-Oriented. Munich: Zuckschwerdt; 2001). The lower the afterload, the more blood the heart will eject with each contraction.

"Pressure Overload" refers to the pathological state of cardiac muscle in which it has to contract while experiencing an excessive afterload. "Right ventricular pressure overload" is characterized by high blood pressure in the pulmonary artery (the artery carrying blood from the right ventricle of the heart to the lungs for oxygenation). Right ventricular pressure overload can occur in acute or chronic settings and can be caused by conditions such as PH and pulmonary stenosis.

"Right ventricular dysfunction due to pressure overload" is the inability of the RV to maintain normal or adequate hemodynamic parameters. Section 4 in Marc A. Simon and Michael R. Pinsky, "Right Ventricular Dysfunction and Failure in Chronic Pressure Overload," Cardiology Research and Practice, vol. 2011, discusses methods of measuring RV dysfunction.

Cardiac "contractility" is the intrinsic ability of heart muscle to generate force and to shorten, ideally autonomously of changes in heart rate (HR), preload or afterload. In that respect, cardiac chamber pressure-volume measurement is the most reliable index for assessing myocardial contractility in the intact circulation, being almost insensible to changes in preload and afterload. Direct measurement of contractility by pressure volume curves is difficult in the clinical setting; indirect measures include echocardiographic determination of ejection fraction, measurement of cardiac output, stroke volume and right as well as left ventricular stroke work index in relation to systemic and pulmonary vascular resistance (http://www.transonic.com/resources/research/understanding-contractility-cardiac-intropy/).

"Cardiac remodeling" refers to genome expression, molecular, cellular and interstitial changes that are manifested clinically as changes in the size, shape and function of the heart (Cohn J, Ferrari R, Sharpe N., *J Am Coll Cardiol.* 2000; 35(3):569-582).

"RV adaptive compensation/RV compensatory remodeling" refers to beneficial remodeling of the RV that allows the ventricle to adapt to an increase in afterload while maintaining efficient contractile function (or contractility). For example, the RV can adapt through eccentric hypertrophy— by adding new sarcomeres in series to increase contractility and increase chamber volume to maintain cardiac output and by increasing vascularity and hence oxygenation of the myocardium. An increased RVLW (right ventricle lateral wall) thickness but constant or reduced RVID:LVID (right to left ventricle internal diameters) ratio is an indicator of adaptive compensatory RV "Pathological remodeling" refers to structural changes in the heart that are associated with cardiac dysfunction. This can include enlargement of the heart and reduction in contractility. The remodeling can include concentric hypertrophy (addition of sarcomeres in parallel and thickening of the ventricle wall with concurrent reduction in chamber size/volume capacity) cardiomyocyte loss through apoptosis, accumulation of excess extracellular matrix (fibrosis), metabolic derangement, insulin resistance and lipotoxicity (Jana S. Burchfield, Minn. Xie and Joseph A. Hill, Circulation. 2013, 128:388-400. Ventricle wall thickness: used to assess myocardial hypertrophy. An increased ratio of the right to left ventricle internal diameters (RVID/LVID) is an indicator of RV pathologic remodeling, as is loss of vascularity which is indicated by a reduction in the number of CD31 positive capillaries "Hypertrophy" is a term used to indicate increase in size of an organ (heart, ventricles), a tissue (muscle) or cells (cardiomyocytes). RV hypertrophy (RVH) may be defined as an RV anterior thickness of greater than or equal to 3.1 mm/m2 in men and greater than or equal to 3.0 mm/m2 in women (J. of Hypertension, 2009, 27(4):854).

"RV failure/Right Heart Failure": RV failure occurs when contractility of the RV is insufficient to compensate for the increase in pulmonary vascular resistance, or RV afterload, and RV-pulmonary artery (PA) uncoupling occurs (Aguero et al. American Journal of Physiology-Heart and Circulatory Physiology Published 15 Oct. 2014 Vol. 307 no. 8, H1204-H1215). Pathologic cardiomyocyte growth, abnormal calcium handling, and increased apoptosis as well as RV ischemia and neuro-hormonal activation have all been identified as mechanisms that promote RV transition to failure.

RV function/dysfunction is most typically assessed clinically by echocardiography and magnetic resonance imaging.

"Eccentric Hypertrophy":increase in ventricular wall thickness through addition of sarcomeres in series, resulting in an increase in the heart's muscle mass and pumping ability.

"Concentric Hypertrophy":increase in ventricular wall thickness through addition of sarcomeres in parallel, resulting in an increase in the heart's muscle stiffness and reduction in compliance.

CT-1 (Cardiotrophin-1) Polypeptides

In accordance with the present invention, CT-1 refers to a mammalian CT-1 (also known as cardiac hypertrophy factor, or CHF). A number of cardiotrophin proteins are known in the art, for example, but not limited to mouse CT-1 (Pennica, D., et al., Proc. Natl. Acad. Sci. USA, 92:1142-1146) and human CT-1 (Pennica, D., et al., (1996). Cytokine, 8:183-189).

CT-1 may be provided as a polypeptide. The sequences of various CT-1 proteins are known in the art and can be used as a basis for the preparation of CT-1 polypeptides (for example, those provided by the above references and GenBank Accession Nos AAC52173 and NP031821 (mouse); and AAD12173 and AAA85229 (human)).

The present invention also contemplates recombinant CT-1, polypeptide analogues, derivatives and variants of the naturally occurring (wild-type) form of CT-1 as well as active peptide fragments of CT-1, and analogues, variants and peptidomimetic forms of the peptide fragments.

A "recombinant protein" is a protein encoded by a gene, recombinant DNA, that has been cloned in a system that supports expression of the gene and translation of messenger RNA.

Active fragments are fragments of the naturally occurring (or wild-type) protein that retain substantially the same activity as the wild-type protein. Fragments typically are at least about 20 amino acids long. In one embodiment of the present invention, the fragments are at least about 50 amino acids long. In another embodiment, the fragments are at least about 70 amino acids long. In a further embodiment, the fragments are at least about 100 amino acids long. In still another embodiment, the fragments are at least about 150 amino acids long. The term "fragment" also encompasses polypeptides corresponding to the wild-type protein that contain a deletion of 1 to about 50 amino acids from the N-terminus, C-terminus or both the N- and C-termini of the wild-type sequence. Candidate fragments can be selected from random fragments generated from the naturally occurring protein or can be specifically designed. The activity of the fragments is tested and compared to that of the wild-type protein and those fragments with substantially the same activity as the naturally occurring protein are selected. Methods for generating polypeptide fragments are well known in the art and include enzymatic, chemical or mechanical cleavage of the wild-type protein or a recombinant version thereof, expression of nucleic acids encoding such fragments, and the like.

As is known in the art, analogues and derivatives of polypeptides, and peptidomimetic compounds may have significant advantages over the naturally occurring forms, including, for example, greater chemical stability, increased resistance to proteolytic degradation, enhanced pharmacological properties (such as, half-life, absorption, potency and efficacy), altered specificity (for example, a broad-spectrum of biological activities) and/or reduced antigenicity. For example, PEGylation of CT1 has been shown to increase its pharmacokinetic property (see U.S. Ser. No. 13/983,282).

A "derivative" is a polypeptide or peptide containing additional chemical or biochemical moieties not normally a part of a naturally occurring sequence. Derivatives include polypeptides and peptides in which the amino-terminus and/or the carboxy-terminus and/or one or more amino acid side chain has been derivatized with a suitable chemical substituent group, and peptides, polypeptides and peptides fused to other proteins or carriers, glycosylated or phosphorylated polypeptides and peptides, polypeptides and peptides conjugated to lipophilic moieties (for example, caproyl, lauryl, stearoyl moieties) and polypeptides and peptides conjugated to an antibody or other biological ligand.

Examples of chemical substituent groups that may be used to derivatize polypeptides and peptides include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy (benzyl-O—CO-), monomethoxysuccinyl, naphthyl-NH—CO—, acetylaminocaproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

An "analogue" is a polypeptide/peptide comprising one or more non-naturally occurring amino acid. For example, a polypeptide/peptide analogue of the invention may have one or more amino acid residues replaced by the corresponding D-amino acid residue or with another non-naturally occurring amino acid. Examples of non-naturally occurring amino acids include, but are not limited to, N-.alpha.-methyl amino acids, C-.alpha.-methyl amino acids, .beta.-methyl amino acids, (.beta.-alanine ((.beta.-Ala), norvaline (Nva), norleucine (Nle), 4-aminobutyric acid (.gamma.-Abu), 2-aminoisobutyric acid (Aib), 6-aminohexanoic acid (.epsilon.-Ahx), ornithine (orn), hydroxyproline (Hyp), sarcosine, citrulline, cysteic acid, cyclohexylalanine, .alpha.-amino isobutyric acid, t-butylglycine, tbutylalanine, 3-aminopropionic acid, 2,3-diaminopropionic acid (2,3-diaP), phenylglycine, 2-naphthylalanine (2-Nal), 1,2,3,4-tetrahydroisoquinoline-3-carboxylic acid (Tic), .beta.-2-thienylalanine (Thi), methionine sulphoxide (MSO) and homoarginine (Har).

As is known in the art, substitution of all D-amino acids for all L-amino acids within a peptide can result in an "inverso" peptide, or in a "retro-inverso" peptide (see Goodman et al. "Perspectives in Peptide Chemistry" pp. 283-294 (1981); U.S. Pat. No. 4,522,752), both of which are considered to be analogues in the context of the present invention. An "inverso" peptide is one in which all L-amino acids of a sequence have been replaced with D-amino acids, and a "retro-inverso" peptide is one in which the sequence of the amino acids has been reversed ("retro") and all L-amino acids have been replaced with D-amino acids. For example, if the parent peptide is Thr-Ala-Tyr, the retro form is Tyr-Ala-Thr, the inverso form is thr-ala-tyr, and the retro-inverso form is tyr-ala-thr (lower case letters indicate D-amino acids). Compared to the parent peptide, a retro-inverso peptide has a reversed backbone while retaining substantially the original spatial conformation of the side chains, resulting in an isomer with a topology that closely resembles the parent peptide.

Peptidomimetics are compounds that are structurally similar to polypeptides/peptides and contain chemical moieties that mimic the function of the polypeptide or peptide of the invention. For example, if a polypeptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere," as used herein, refers to a chemical structure that can be substituted for a polypeptide or peptide because the steric conformation of the chemical structure is similar to that of the peptide or polypeptide, for example, the structure fits a binding site specific for the polypeptide or peptide. Examples of peptidomimetics include peptides comprising one or more backbone modifications (i.e., amide bond mimetics), which are well known in the art. (see, for example, Spatola, Vega Data Vol. 1, Issue 3, (1983); Spatola, in Chemistry and Biochemistry of Amino Acids Peptides and Proteins, Weinstein, ed., Marcel Dekker, N.Y., p. 267 (1983); Morley, J. S., Trends Pharm. Sci. pp. 463-468 (1980); Hudson et al, Int. J. Pept. Prot. Res. 14:177-185 (1979); Spatola et al., Life Sci. 38:1243-1249 (1986); Hann, J. Chem. Soc. Perkin Trans. 1307-314 (1982); Almquist et al., J. Med. Chem. 23:1392-1398 (1980); Jennings-White et al., Tetrahedron Lett. 23:2533 (1982); Szelke et al., EP 45665 (1982); Holladay et al., Tetrahedron Lett. 24:4401-4404 (1983); and Hruby, Life Sci. 31:189-199 (1982)). Other examples of peptidomimetics include peptides substituted with one or more benzodiazepine molecules (see, for example, James, G. L. et al. (1993) Science 260:1937-1942) and peptides comprising backbones cross-linked to form lactams or other cyclic structures.

One skilled in the art will appreciate that not all amino acids in a peptide or polypeptide need be modified. Similarly not all amino acids need be modified in the same way. Polypeptide/peptide derivatives, analogues and peptidomimetics of the present invention thus include chimeric molecules that contain two or more chemically distinct regions, each region comprising at least one amino acid or modified version thereof.

A variant polypeptide or peptide is one in which one or more amino acid residues have been deleted, added or substituted for those that appear in the amino acid sequence of the naturally occurring protein. In the context of the present invention, a variant also retains substantially the same activity as the naturally occurring protein. Typically, when a variant contains one or more amino acid substitutions they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

In accordance with the present invention, an analogue, derivative, variant or active fragment has substantially the same or increased activity as compared to a naturally occurring CT-1 protein. The term "substantially identical activity" indicates an activity that is about 50% of the activity of a naturally occurring CT-1 protein. In one embodiment, substantially identical activity indicates an activity that is about 60% of the activity of a naturally occurring CT-1 protein. In another embodiment, it indicates an activity that is about 75% of the activity of a naturally occurring CT-1 protein. In still another embodiment, the analogue, derivative, variant or active fragment exhibits enhanced (increased) activity compared to a naturally occurring CT-1 protein, preferably a human CT-1 protein. Activity of CT-1 can be determined by, for example, measuring its ability to promote STAT3 phosphorylation and transcriptional activity. Methods of measuring increases in STAT3 phosphorylation and transcriptional activity are known in the art and include those provided herein.

The polypeptides of the present invention can be prepared by methods known in the art, such as purification from cell extracts or the use of recombinant techniques. Shorter sequences can also be chemically synthesised by methods known in the art including, but not limited to, exclusive solid phase synthesis, partial solid phase synthesis, fragment condensation or classical solution synthesis (Merrifield (1963) J. Am. Chem. Soc. 85:2149; Merrifield (1986) Science 232:341). The polypeptides of the present invention can be purified using standard techniques such as chromatography (e.g. ion exchange, affinity, and sizing column chromatography or high performance liquid chromatography), centrifugation, differential solubility, or by other techniques familiar to a worker skilled in the art.

The polypeptides can also be produced by recombinant techniques. Typically this involves transformation (including transfection, transduction, or infection) of a suitable host cell with an expression vector comprising a polynucleotide encoding the protein or polypeptide. The nucleic acid sequences for various CT-1 genes are known in the art (see for example, Pennica et al. Ibid., U.S. Pat. Nos. 5,723,585; 5,679,545, 5,627,073 (mouse) and GenBank Accession Nos. Q16619 and NM.sub.001330 (human)) and may be used as a basis for the polynucleotides of the invention.

The polynucleotides can be derived or purified from a suitable source by standard techniques. The polynucleotides can be genomic DNA or RNA or they can be cDNA prepared from isolated mRNA. Alternatively, the known sequences may be used to prepare probes to obtain other nucleic acid sequences encoding a CT-1 polypeptide from various sources using standard techniques. Suitable sources for obtaining the nucleic acids are those cells which are known to express the proteins of the invention, such as cardiomyocytes, as well as skeletal muscle tissue and other tissues with measurable CT-1 transcripts.

Polynucleotides encoding fragments or variants of the naturally occurring CT-1 proteins can be constructed by deletion, addition, and/or substitution of one or more nucleotides within the coding sequence using standard techniques, such as site-directed mutagenesis techniques.

Suitable expression vectors for use with the nucleic acid sequences of the present invention include, but are not limited to, plasmids, phagernids, viral particles and vectors, phage and the like. For insect cells, baculovirus expression vectors are suitable. For plant cells viral expression vectors (such as cauliflower mosaic virus and tobacco mosaic virus) and plasmid expression vectors (such as the Ti plasmid) are suitable. The entire expression vector, or a part thereof, can be integrated into the host cell genome. In some circumstances, it is desirable to employ an inducible expression vector as known in the art.

Those skilled in the field of molecular biology will understand that a wide variety of expression systems can be used to provide the recombinant polypeptide or peptide. The precise host cell used is not critical to the invention. The polypeptide or peptide can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley &; Sons, N.Y.; and various expression vectors may be chosen from those provided, e.g., in Cloning Vectors: A Laboratory Manual (Pouwels et al., 1985, Supp. 1987) and by various commercial suppliers.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed heterologous protein.

The host cells harbouring the expression vehicle can be cultured in conventional nutrient media adapted as needed for activation of a chosen gene, repression of a chosen gene, selection of transformants, or amplification of a chosen gene according to known procedures.

CT-1 (Cardiotrophin-1) Polynucleotides

The present invention also contemplates administration of polynucleotides encoding CT-1 (or a variant or active fragment thereof, or an activator of CT-1) which then express the encoded product in vivo, by various "gene therapy" methods known in the art. Methods of administering CT-1 via a polynucleotide are known in the art. For example, CT-1 has been used in an adenovirus to treat motor neuron degeneration (Lesbordes et al., (2003), Hum. Molec. Gen. 12, 1223-1229). Gene therapy includes both ex vivo and in vivo techniques. Thus host cells can be genetically engineered ex vivo with a polynucleotide, with the engineered cells then being provided to a patient to be treated.

Alternatively, cells can be engineered in vivo by administration of the polynucleotide using techniques known in the art. For example, by direct injection of a "naked" polynucleotide (Feigner and Rhodes, (1991) Nature 349: 351-352; U.S. Pat. No. 5,679,647) or a polynucleotide formulated in a composition with one or more other agents which facilitate uptake of the polynucleotide by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the polynucleotide with lipids, cell-surface receptors or transfecting agents; by encapsulation of the polynucleotide in liposomes, microparticles, or microcapsules; by administration of the polynucleotide linked to a peptide which is known to enter the nucleus, or by administration of the polynucleotide linked to a ligand subject to receptor-mediated endocytosis (see, for example, Wu and Wu, (1987) J. Biol. Chem. 262:4429-4432), which can be used to target cell types specifically expressing the receptors.

Alternatively, a polynucleotide-ligand complex can be formed in which the ligand comprises a fusogenic viral peptide to disrupt endosomes, allowing the polynucleotide to avoid lysosomal degradation; or the polynucleotide can be targeted for cell specific uptake and expression in vivo by targeting a specific receptor (see, for example, International Patent Applications WO 92/06180, WO 92/22635, WO92/20316, WO93/14188 and WO 93/20221). The present invention also contemplates the intracellular introduction of the polynucleotide and subsequent incorporation within host cell DNA for expression by homologous recombination (see, for example, Koller and Smithies (1989) Proc. Natl. Acad. Sci. USA 86; 8932-8935; Zijlstra et al. (1989) Nature 342:435-438).

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)). The expression vector may be a plasmid vector or a viral-based vector. The polynucleotide is usually incorporated into the vector under the control of a suitable promoter that allows for expression of the encoded polypeptide in vivo. Suitable promoters are known in the art.

Pharmaceutical Compositions

The present invention further provides pharmaceutical compositions comprising CT-1 (such as recombinant hCT-1), an analogue, derivative, variant or active fragment thereof, an activator of CT-1 or a CT-1 inhibitor, a CT-1 polynucleotide or a CT-1 polynucleotide incorporated into a vector, or an engineered cell, and a pharmaceutically acceptable diluent or excipient. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000).

The pharmaceutical composition of the present invention may further comprise one or more conventional pharmaceutically acceptable excipients. Pharmaceutically acceptable excipients for various different dosage forms are well-known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) is (are) selected based in part on the dosage form, the intended mode of administration, the intended release rate, and manufacturing reliability. Examples of common types of excipients include various polymers, waxes, calcium phosphates, sugars, etc.

Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is pharmaceutically acceptable oil typically used for parenteral administration.

The pharmaceutical compositions of the present invention may be formulated into various types of dosage forms. As used herein, the term "dosage form" refers to a pharmaceutical composition comprising a solid formulation as described herein, together with one or more additives, in a form or device suitable for non-intravenous administration to a patient. Examples include, but are not limited to tablets, including rapid disintegrating tablets, caplets, capsules, sachet formulations, solutions, suspensions, emulsions, creams, gels, hydrogels, films, lozenges, chewing gum, pastes, ointments, sprays, aerosol inhalers, dry powder inhalers, suppositories, pessaries, enemas, and the like.

Solid oral dosage forms include tablets. The tablet is preferably a swallowable tablet. It may optionally be coated with a film coat comprising, in essence, any suitable inert coating material known in the art. The above lists of excipients and forms are not exhaustive.

Administration

Administration of the pharmaceutical compositions may be via a number of routes depending upon whether local or systemic treatment is desired and upon the area to be treated. Administration may be orally, sublingually, rectally, nasally, vaginally, topically (including the use of a patch or other transdermal delivery device), by pulmonary route (e.g. by inhalation or insufflation of powders or aerosols, including by nebulizer), or parenterally. Also contemplated are intratracheal, intranasal, epidermal and transdermal administration. Parenteral administration includes subcutaneously, intravenous, intraarterial, subcutaneous, intraperitoneal or intramuscular injection, for example, but not limited to intracardial injection (for example using a percutaneous transendocardial catheter system) or infusion, or intracranial, e.g. intrathecal or intraventricular administration.

Bioscaffolds are also known to deliver biological materials to target tissues (see EP 1 827 577 B1 for example) and are also contemplated. The scaffold is designed to deliver the polypeptides of the invention or polynucleotides that encode such peptides to the bodily targets. For instance, the scaffold could be designed to provide slow release of CT-1 protein from biomaterial patches on the heart.

The compositions of the present invention may be delivered in combination with a pharmaceutically acceptable vehicle. Preferably, such a vehicle would enhance the stability and/or delivery properties. Examples include liposomes, microparticles or microcapsules. In various embodiments of the invention, the use of such vehicles may be beneficial in achieving sustained release of the active component.

When formulated for parenteral injection, the pharmaceutical compositions are preferably used in the form of a sterile solution, containing other solutes, for example, enough saline or glucose to make the solution isotonic.

For administration by inhalation or insufflation, the pharmaceutical compositions can be formulated into an aqueous or partially aqueous solution, which can then be utilised in the form of an aerosol.

For the oral mode of administration, the compounds of the invention are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added.

For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include the obroma oil, glycerinated gelatin, hydrogenated vegetable oils, mixtures of polyethylene glycols of various molecular weight and fatty acid esters of polyethylene glycol. Analogous gels or creams can be used for vaginal, urethral and rectal administrations.

Numerous administration vehicles will be apparent to those of ordinary skill in the art, including without limitation slow release formulations, liposomal formulations and polymeric matrices.

The dosage requirements for the pharmaceutical compositions vary with the particular compositions employed, the route of administration and the particular subject being treated. Dosage requirements can be determined by standard clinical techniques known to a worker skilled in the art. Treatment will generally be initiated with small dosages less than the optimum dose of each compound. Thereafter the dosage is increased until the optimum effect under the circumstances is reached. In general, the pharmaceutical compositions are administered at a concentration that will generally afford effective results without causing any harmful or deleterious side effects. Administration can be either as a single unit dose or, if desired, the dosage can be divided into convenient subunits that are administered at suitable times throughout the day.

Kits

The present invention additionally provides for therapeutic kits containing CT-1, an analogue, derivative, variant or active fragment thereof, or an activator of CT-1, a CT-1 polynucleotide or a CT-1 polynucleotide incorporated into a vector, or an engineered cell. Kits comprising one or more CT-1 inhibitors in pharmaceutical compositions are also provided. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient.

The components of the kit may also be provided in dried or lyophilised form and the lit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or any such medically approved delivery vehicle.

In another aspect of the invention, there are provides commercial packages and kits comprising a non-intravenous dosage form as described herein, together with one or more instructions for use in the treatment or prevention of a disease or condition.

The dosage form and, optionally, other components of the kit or commercial package, may be packaged in an appropriate container and, associated with such containers, can be a notice in the form prescribed by a governmental agency regulating the manufacture, use or sale of pharmaceutical or biological products, which notice reflects approval by the agency of manufacture, use or sale for human or animal administration.

When the components of the kit or commercial package may be provided in one or more liquid solutions, the liquid solution can be an aqueous solution or suspension, for example, a sterile aqueous solution or suspension. In this case the container means may itself be an inhaler, syringe, pipette, eye dropper, nasal dropper, ear dropper, or other such like apparatus, from which the formulation may be administered to a patient. The container may also be a dry powder inhaler.

Irrespective of the number or type of containers, the kit or commercial package may comprise an instrument for assisting with the administration of the composition to a patient. Such an instrument may be an inhalant, syringe, pipette, forceps, measured spoon, eye dropper or any such medically approved delivery vehicle.

EXPERIMENTAL

Applicant's observations demonstrate that cardiomyocytes treated with recombinant human CT1 protein (hCT1) engage a form of adaptive and compensatory remodeling that resembles a physiologic growth response, adding sarcomeres in series, a cellular/molecular change that is fully reversible with the removal of hCT1. hCT1 administration also overrides concurrent signals that propel pathologic hypertrophy (such as isoproterenol/phenylephrine). In addition, Applicant has demonstrated that in vivo delivery of recombinant hCT1 leads to a rapid (14 days) alteration in the structure of the heart, with volume and wall dimension changes characteristic of physiological cardiac adaptation, such as to exercise, which is a fully reversible response following cessation of hCT1 delivery. hCT1 administration was shown to improve cardiac contractile performance in a model of progressive right heart failure (pulmonary hypertension), demonstrating the clinical utility of this protein in an otherwise intractable cardiac disease state.

Recombinant hCT-1 was manufactured using methods known the art. The 201 amino acid sequence is reflected in GenBank Accession Nos AAD12173 and AAA85229 (human).

Example 1: The Effects of hCT-1 Protein on Cardiomyocyte Growth and Morphology

Phenylephrine (PE) was used as a pathological adaptive compensation control as it is a known target of the stress-activated G-protein coupled alpha (α)-adrenergic pathway. Primary neonatal cardiomyocytes were stimulated for 24 hours with hCT1 (0.5 nM), PE (100 μM), the combination of hCT1 and PE, or control serum-free (SF) media followed by morphometric analysis (cell area and length:width ratio) (FIG. 1A). Treatment with hCT1, PE and hCT1+PE resulted in cardiomyocyte cell growth, with respective cell areas increases of 162%, 171%, and 112% respectively. However, stimulation with hCT1 or hCT1+PE resulted in an eccentric/elongated growth (elongated-increased length to width ratio; L:W ratio of 172% and 120%) whereas stimulation with PE, which is a known pathological stimulus, induced concentric growth of cardiomyocytes (cuboidal—same or shortened L:W ratio)(FIG. 1B) . . . . Moreover, the morphology of cardiomyocytes exposed to PE shifted from concentric to eccentric upon pre-treatment with CT-1, suggesting that CT-1 exerts a dominant effect over pathological stimulation with PE (FIG. 1A). This CT-1 mediated growth is typical of the cardiomyocyte adaptations that occur during physiologic adaptive compensation with an L:W ratio that is divergent from PE induced growth. These data also suggest CT-1 limits or reduces the activity of factors that promote pathologic myocyte hypertrophy.

Figure 2B:
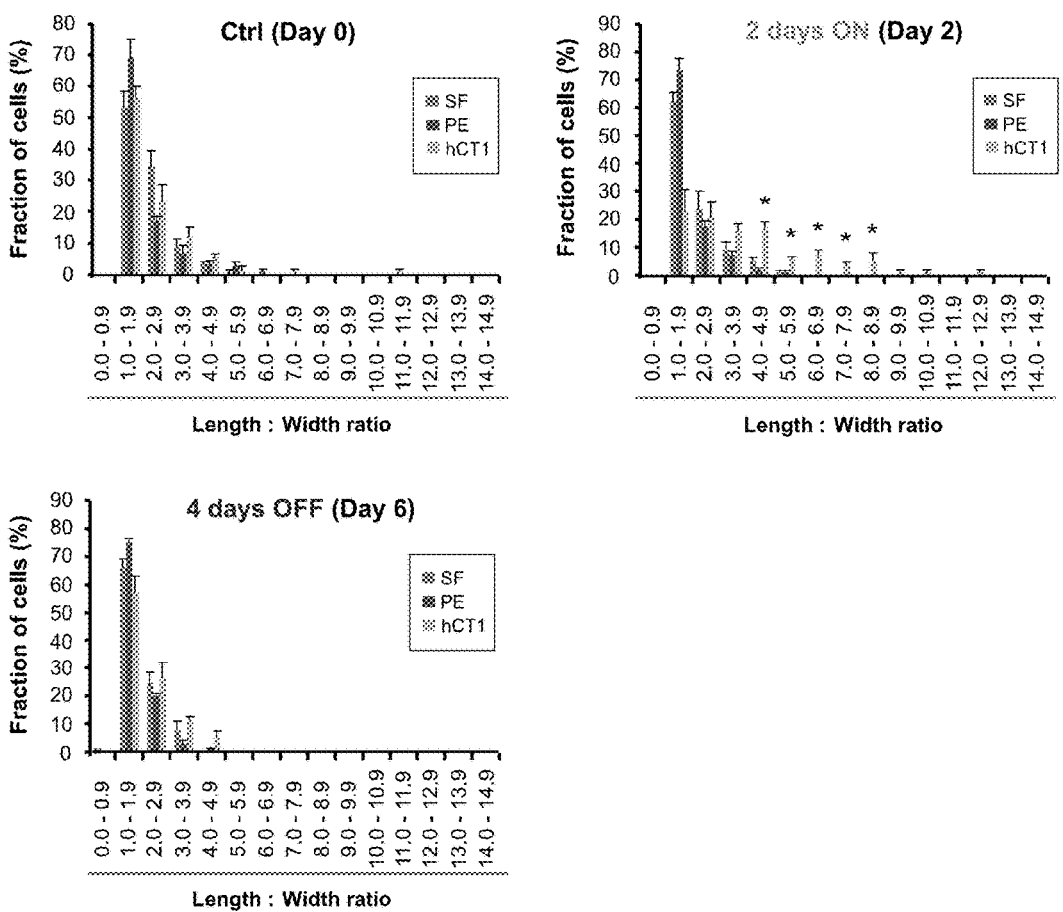

Example 2: hCT-1 Induces a Physiological and Reversible Cardiomyocyte Hypertrophy In Vitro The morphological effects of CT-1 in an in vitro reversion setting (FIGS. 2A and 2B) were explored. Primary neonatal cardiomyocytes were stimulated for 2 days with phenylephrine (PE, 100 μM) or hCT1 (0.5 nM) followed by removal of the stimulus for 4 days: i.e. replenished with serum-free (SF) media. Cells were imaged at Day 0 and Day 2 of stimulation; and at Day 6 (4 days post-treatment). Both PE and hCT1 induced an increase in cardiomyocyte cell size after 2 days of stimulation compared to control (Ctrl) cells (n=3; * and **, $P<0.05$). Interestingly, a 2 day treatment with CT-1 protein followed by removal of the cytokine (CT-1) for a further 4 day period, resulted in reversion of the myocyte hypertrophy (cell area) of primary cardiomyocytes (FIG. 2A). This reversion in CT-1 mediated growth was in contrast to the effects of PE (pathologic hypertrophy agonist), where PE treated cardiomyocytes remained hypertrophied despite the removal of the agonist (FIG. 2A). The population frequencies of L:W ratios of cardiomyocytes stimulated as above were examined (FIG. 2B). The data indicates that under control (Ctrl i.e. non-stimulated conditions), the majority of cardiomyocytes (~60%) display a L:W ratio of between 1.0 to 2.0. However, upon treatment with CT-1, only ~20% of cardiomyocytes display a L:W ratio of 1.0 to 2.0 with the remaining cardiomyocytes showing an increased shift between 3.0 and 9.0 indicating eccentric growth. Finally, after removing CT-1 stimulation for 4 days, reversion of L:W ratio occurs and a similar population frequency to that with non-stimulated controls is seen. Of note, stimulation with PE resulted in a similar frequency of L:W ratios to that observed with the control myocytes throughout the course of the experiment. These observations indicate that although there is not complete penetrance of the eccentric growth (presumably due to the dosage and timing of CT-1 stimulation used), CT-1 causes an eccentric and reversible cardiomyocyte growth similar to what is seen during RV adaptive compensation, which is distinct from the concentric growth observed with PE which models pathological hypertrophic changes.

Example 3: hCT-1 Induces a Reversible Left Ventricular Adaptive Myocardial Remodeling In Vivo CT-1 was tested in vivo to determine whether its administration would induce a myocardial adaptive remodeling characteristic of physiologic compensation (FIGS. 3A, 3B, and 3C). Osmotic minipumps containing PBS control (Ctrl) or hCT1 (6 μg/kg/hr) or Isoproterenol (ISO, 1 mg/kg/day) were implanted subcutaneously in rats. ISO is a beta-adrenergic receptor agonist and continuous infusion with ISO in rats is known to induce pathological cardiac hypertrophy and cardiomyocyte damage (in both the right and left ventricles) which progresses to heart failure (Morisco et al (2001) J Mol Cell Cardiol 33:561-573 and Grimm et al (1998) Cardiovascular Research 37:91-100). After 2 weeks of treatment, M-mode ECHO analysis was used to assess myocardial structure/function (FIG. 3A). In this model, an increased right ventricle lateral wall (RVLW) thickness indicates the presence of myocardiocytes growth, and an increased ratio of the right to left ventricle internal diameters (RVID/LVID) is an indicator of pathologic hypertrophy. An increased RVLW thickness but constant or reduced RVID:LVID ratio is an indicator of adaptive compensatory RV remodeling. Both hCT1 and ISO induced a significant increase in RVLW thickness (12% and 32% fold increase, respectively) compared to control rats (n=3; * and **, $P<0.05$). However, only rats treated with ISO displayed the expected increase (24%) in the RVID/LVID ratio (n=3; #, $P<0.05$); whereas hCT1 treated rats did not develop this pathologic state of cardiac hypertrophy (FIG. 3B). An in vivo growth reversal analysis was also conducted. Following a 2 week delivery of CT-1 protein (6 μg/kg/hr) or PE (10 mg/kg/day) as the pathologic control in this case, animals were then assessed for cardiac structure/function at a 6 week follow-on period. At 2 weeks, both CT-1 and PE induced an increase in (both) ventricle wall thickness. Remarkably, at 6 weeks post-treatment, CT-1 treated animals displayed a complete return to baseline cardiac dimensions for wall thickness comparable to that observed in the control treated rats (FIG. 3C). However, the transient delivery of PE over an initial 2 week period led to a sustained alteration in cardiac dimensions following a 6 week recovery time, retaining the substantial increase in wall thickness. Notably, the PE treated rats had maintained their increased RVID/LVID ratio (and increased heart weight to body weight ratio) at 6 weeks post-treatment compared to control rats, a phenotype indicative of pathologic hypertrophy (FIG. 4A). Furthermore, at 6 weeks post-treatment, the PE treated rats showed a significant decrease in cardiac capillary density (i.e. decreased blood supply to the myocardium) compared to CT-1 treated and control animals—quantified from CD31 immunostained sections of right ventricles (FIG. 4B), further showing the sustained pathological response to PE and return to normal parameters after withdrawal of CT1 treatment. Collectively, these studies support the contention that CT-1 elicits a reversible physiologic cardiac adaptive compensation.

Example 4: Human Cardiotrophin-1 (hCT1) Improves RV Adaptation in Response to Increase Afterload Caused by Severe Pulmonary Hypertension (PH) in Fischer Rats Given that CT-1 induces phenotypic characteristics associated with beneficial RV physiologic adaptive compensation, a prediction was made by the Applicants that CT-1 would enhance RV adaptation to increased afterload in a disease setting. This supposition was tested to examine whether CT-1 protein can improve the ability of the RV to functionally adapt and limit or reduce right heart failure that is associated with pulmonary arterial hypertension (PAH), a form of PH caused by abnormalities in the lung vasculature (FIGS. 5A and 5B). PAH has a highly tractable and reproducible rodent equivalent, the SU5146/hypoxia rat model, which recapitulates many key aspects of the disease including progressive right heart failure in the Fischer CDF™ rat strain, a feature that is not observed in the Sprague Dawley strain in the same model of PH. Use of this PH model offers a clear advantage in providing an accurate preclinical disease setting to test the utility of CT-1, rather than simply testing co-administration of CT-1 with general alpha-adrenergic stimulants such as PE or ISO in vivo. While in vitro testing of these standard stimulants does have considerable merit as a means to address mechanism of action, these compounds do not have the direct disease relevance associated with use of the PH model. Also, right heart failure drives symptoms and prognosis in many forms of PH, including in Group 2 PH caused by increases in left ventricular filling pressures, of which heart failure with preserved ejection fraction (HFpEF) is an important example which is increasingly recognized as one of the greatest therapeutic challenges in clinical cardiology today. PH was induced by administering a single subcutaneous injection of SU5416 (20 mg/kg) to Fischer CDF™ rats followed by exposure to chronic hypoxia (8-10% $O_2$) for 3 weeks. After these 3 weeks, rats were recovered for 24 hours in normoxia before implantation of PBS filled (control) or hCT-1 filled (6 µg/kg/hr delivery) osmotic minipumps. Control rats were exposed to normoxic conditions throughout the study and only treated with PBS (FIG. 5A). Echocardiography analyses were conducted weekly and the following parameters were measured: Right Ventricle Posterior Wall thickness (RVPW), Ratio of Right Ventricle Internal Diameter to Left Ventricle Internal (RVID/LVID), Pulmonary Artery Acceleration Time (PAAT), Fractional Area Change (FAC), and Cardiac Output (CO). At 3 weeks (prior to pump implantation), there was already a marked and significant increase in the RVID/LVID ratio, indicative of developing RV failure in this model of severe PH. In PH animals receiving saline, there was a progressive increase in this ratio over the subsequent 3 weeks, associated with other evidence of progressive RV failure, such as worsening contractile function (Fractional Area Shortening) and reductions in cardiac output. Administration of CT-1 beginning at 3 weeks resulted in a progressive improvement in the RVID/LVID ratio over 3 weeks, indicative of RV adaptation, associated with improvements in contractile function and cardiac output (FIG. 5B). Moreover, this correction in right heart failure occurred without any alteration in the RV afterload, assessed by measurement of right ventricular systolic pressure (RVSP), although there was a significant decrease in right atrial pressure (RAP) in CT-1 treated animals, consistent with an improvement in right heart failure due to better RV compensatory adaptation. These data strongly suggest that CT-1 elicits the beneficial effect by directly targeting the RV myocardium and inducing adaptive RV remodeling. This indicates that CT-1 acts directly on the RV to exert its beneficial effect. CT-1 does not limit the lung pathology that is the primary driver of this model, confirming the cardiac specific impact of CT-1.

Example 5: Physiologic/Beneficial Compensatory Remodeling with hCT1 Activates a Transcriptional and Signaling Program Distinct from that Seen in Pathological Hypertrophy The signaling pathways that CT-1 engages in mediating physiologic adaptive compensatory remodeling were examined. The applicants predicted that cardiomyocyte adaptive remodeling mediated by CT-1 results (in part) from the induction of a specific transcriptional program, which is distinct from that of pathologic hypertrophic response. To address this hypothesis, the applicants tested the activity of two well-known transcription factor families that have been linked to both physiologic and pathologic cardiomyocyte growth, the Mef2 (Kolodziejczyk et al. 1999 Curr Biol. 9, 1203-1206; Kim et al. 2008, J Clin Invest. 118, 124-132.) and the NF-κB family (Gordon et al. 2011, Circ Res. 108, 1122-1132). Primary neonatal cardiomyocytes were transfected with luciferase reporter plasmids (NF-κB and Mef2) to be used as a read out of transcriptional activity. Luciferase activity was determined after treatments for 24 hrs with: hCT1 (0.5 nM), PE (100 µM), or procaspase 3 activating compound 1, PAC-1 (25 µM). Treatments at early timepoints (30 min, 1 hr, and 3 hr) were also conducted for hCT1 (FIGS. 6A, 6B, and 6C). hCT1 treatment resulted in a significant activation of both NF-κB and Mef2 at 1 hr and 3 hr (n=4; * and **, P<0.05); while at 24 hrs, only NF-κB transcriptional activity was sustained (n=4; #, P<0.05). This pattern of transcription factor activation was distinct from that induced by PE and by the caspase 3 specific activating compound PAC-1. Pathologic hypertrophy stimulation with both PE and PAC-1 caused significant activation of Mef2 after 24 hrs. Moreover, co-stimulation of hCT1/PE and hCT1/PAC-1 led to a significant reduction in the activation of Mef2 compared to PE and PAC-1 alone (n=4; § and §§, P<0.05), suggesting that reduced Mef2 activation and maintenance of NF-κB is involved in promoting adaptive compensatory remodeling.

This also suggests that CT-1 mediated physiologic adaptive compensation is not conducive to sustained Mef2 activity. Moreover, it is reasonable to assume that CT-1 may moderate the activity of additional transcription factors, which further contribute to the adaptive compensation phenotype. As such, Applicants decided to test the hypothesis that STAT3 (Signal transducer and activator of transcription 3) dependent transcriptional activity is a specific determinant for CT-1 induced physiologic adaptive compensation. STAT3 phosphorylation and transcriptional activation is a response that is common to the Interleukin-6 cytokine family (of which CT-1 is a member), which is mediated through binding and activation of a JAK/gp130 (Janus kinase/glycoprotein 30) receptor complex. Importantly, CT-1 is known to engage STAT3 activation in cardiomyocytes and gp130 mediated receptor signalling has been shown to be critical for the survival and post-natal adaptation of cardiomyocytes. Applicants demonstrated that cardiomyocytes transfected with a STAT3 luciferase reporter vector, showed significant STAT3 activation as early as 30 minutes (and up to 24 hours) following CT-1 treatment (n=4; # and *, P<0.05), with only minimal (if any) activation observed following treatment with PE or PAC-1 over the same timepoints (FIG. 6B). Interestingly, co-stimulation with CT-1/PE and CT-1/PAC-1 led to a significant activation of STAT3 compared to PE and PAC-1 alone (n=4; § and §§, P<0.05), suggesting that CT-1 exerts a dominant effect compared to the stimulation with PE or PAC-1.

Given that CT-1 engages a gp130 signaling pathway, it is reasonable to suggest that CT-1 achieves the physiologic cardiac adaptive compensation response by constraining/inhibiting the activity of transcription factors (via direct phosphorylation) that have commonly been associated with the induction of pathological cardiac hypertrophy such as nuclear factor of activated T-cells, N FAT. Applicants tested this supposition by infecting cardiomyocytes with an NFAT luciferase reporter linked to an Adenovirus (AdV) backbone (FIG. 6C). Cardiomyocytes were infected at a Mean of Infectivity (MOI) of 20 with Nfat-AdV for 24 hours prior to stimulation with hCT1 (0.5 nM), PE (100 µM), or procaspase 3 activating compound 1, PAC-1 (25 µM). As an initial positive control, co-infection of NFAT-AdV with activated Calcineurin-AdV (a phosphatase and potent activator of NFAT signalling) caused a significant increase in NFAT activity (n=4; *, P<0.05). Pathologic hypertrophy stimulation with PE or PAC-1 caused a significant increase of NFAT activity as early as 3 hours (up to 24 hours) compared to baseline levels (n=4; § and §§, P<0.05); however, pre-treatment with CT-1 significantly decreased NFAT activity compared to PE or PAC-1 alone at 3 hours and 24 hours (n=4; # and ##, P<0.05). Interestingly, CT-1 stimulation caused a slight, yet significant, decrease in NFAT activity compared to baseline levels at 30 minutes, 1 hour, and 3 hours but not at 24 hours (FIG. 6C). This data indicates that CT-1 has an overall inhibitory effect on NFAT activity. Although the exact mechanism of inhibition is unknown, Applicant has shown CT-1 engaging a PI3K signalling pathway and it would be reasonable to postulate that phosphorylation of NFAT by CT-1/PI3K signalling would limit NFAT activity.

Taken together, these observations provide compelling evidence that physiological cardiac adaptive compensation stimulation with CT-1 engages a unique transcriptional expression pattern that is distinct from pathological stimulation—i.e. sustained activation of NF-κB and STAT3 with limited activation of Mef2 and N FAT.

Example 6: hCT1 Promotes Cardioprotection Against Cytotoxic Hydrogen Peroxide ($H_2O_2$) Stimulation and is PI3K-Dependent To further assess CT-1 cardioprotection, Applicant tested the effects of CT-1 on cardiomyocytes viability upon exposure to hydrogen peroxide ($H_2O_2$)—an exogenous source of free radicals that causes cell death, mimicking the hypoxic conditions observed in certain cardiovascular diseases, including PAH (FIGS. 7A, 7B. and 7C). Cardiomyocytes were treated with control serum-free media or with $H_2O_2$ (300 µM, 1 hr) to induce cell death in the presence or absence of hCT1 (0.5 nM). After 24 hrs, cells were incubated with the cell viability marker Propidium Iodide (PI) (1 µg/mL) and analyzed by FACS (Ex: 535 nm, Em: 617 nm) for viable cells; i.e. cells inside the gated region of the side scatter (SS) versus PI plot (FIG. 7A). As predicted, cardiomyocyte viability at 24 hours (measured by Propidium Iodide staining) was decreased upon 1 hour $H_2O_2$ treatment (300 µM) (24% vs. control); however, a significant increase (~34%) in viability was observed upon pre-treatment with CT-1 (n=4; # and *, P<0.05) (FIG. 7B). To determine a signaling pathway influencing this CT-1 mediated cardioprotection, the phosphoinositide 3-kinase (PI3K) pathway was targeted. The PI3K pathway is a critical feature of physiological cardiac adaptive compensation and is a key protective feature distinguishing it from pathological adaptive compensation. Therefore, cardiomyocytes were pre-treated with a PI3K inhibitor (LY294002, 50 µM) before CT-1/$H_2O_2$ treatment.

A decrease in viability (70% vs. control) was observed with $H_2O_2$ and viability was significantly improved (154% vs. $H_2O_2$) in the presence of hCT1 (n=4; * and #, P<0.05). Furthermore, pre-treatment with LY294002 caused a significant decrease in viability (46%) compared to cells treated only with hCT1/H2O2, indicating a requirement for PI3K signaling in hCT1-mediated cardioprotection (n=4; §, P<0.05) (FIG. 7C).

Example 7: CT-1 as a Pro-Angiogenic Factor in the Adaptive Hypertrophic Response Applicant explored the role of CT-1 as a pro-angiogenic factor in the adaptive hypertrophic response. Physiologic cardiac adaptive compensation is associated with an increase in capillary density, whereas pathologic response is characterized by a decline or no change at all. Importantly, the compensatory vascular growth/angiogenesis that occurs during physiologic adaptive compensation is permissive for the increased workload that accompanies physiologic adaptive compensation. Despite this adaptation, little information exists regarding the mechanisms that match the demand for angiogenesis to the beneficial form of myocardial growth. The rapid in vitro and in vivo adaptive compensation in response to CT-1 supports a hypothesis that the cardiomyocyte itself may act in a paracrine fashion, to signal and promote angiogenesis. To address this conjecture, Applicant examined whether CT-1 treated primary cardiomyocytes produced vascular endothelial growth factor (VEGF), an angiogenic factor known to be produced and secreted by cardiomyocytes. Primary cardiomyocytes were incubated with control serum-free media (Ctrl, SF media) or stimulated with hCT1 (0.5 nM), PE (100 µM), or PAC-1 (25 µM) for 24 hours. Immunofluorescence was used to detect α-actinin, Vascular Endothelial Growth Factor—VEGF, and nuclei. The no primary antibody control shows no non-specific binding/staining. Interestingly, stimulation of primary cardiomyocytes with CT-1 led to a rapid increase in the expression of VEGF, yet treatment with pathologic hypertrophy stimulants such as PE or the caspase 3 agonist PAC-1, resulted in less VEGF expression (FIG. 8A). Based on these observations Applicant next conducted a comparative gene expression analysis of control (non-stimulated) versus CT-1 treated (0.5 nM, 24 hours) primary cardiomyocytes, using the Affymetrix Rat gene 2.0ST array. Bioinformatic analysis of the array experiment (FIG. 8B) revealed a robust induction of a number of angiogenic and endothelial factors including, but not limited to Angiopoietin-like 4 (Angptl4), Fms-related tyrosine kinase 4 (Flt4) and von Willebrand factor 5A (Vwa5a), whereas VEGF displayed a modest increase (1.3 fold). Antimicrobial peptides and PI3K pro-survival receptors were the other families of target genes significantly activated.

Taken together, these data complement our observations of CT-1 is a potent activator of pro-survival and pro-angiogenic signaling pathways in mediating an adaptive physiological cardiac adaptive compensation response.

Example 8: CT-1 Robustly Inhibits P19 Cardiac Differentiation

Figure 9A:
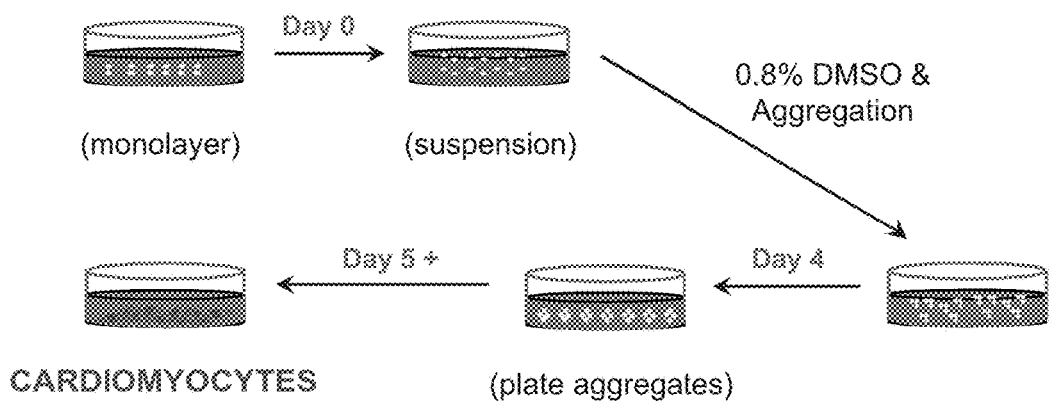
FIGS. 9A, 9B, 9C, and 9D. hCT1 robustly inhibits P19 cardiac differentiation.
Figure 9B:
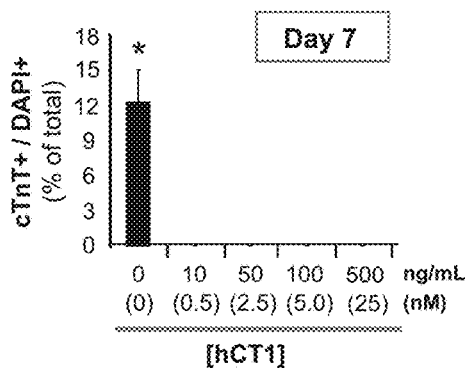

Protection during conditions of cardiac pathologies can be conferred not only by the activation of pro-survival/pro-angiogenic signaling pathways but also by inducing the differentiation of cardiogenic progenitor cells. However, accumulating evidence indicates that the rate at which endogenous cardiogenic progenitor cells give rise to new cardiomyocytes which structurally and functionally integrate into the adult mammalian heart occurs at extremely low levels, and this is unlikely to account for any physiological cardiac adaptation and cardioprotection. To test the effect of CT1 on cardiomyocyte differentiation, undifferentiated cells were induced to undergo cardiac differentiation with 0.8% DMSO and aggregation. At day 0, P19 cells are plated onto non-adherent bacterial petri dishes in the presence of MEMα growth media with 0.8% DMSO (control) or in the presence of different doses of hCT1-containing MEMα media ranging from 0.5 nM (10 ng/mL) to 25 nM (500 ng/mL) with 0.8% DMSO. P19 cells are then allowed to aggregate for 4 days. Finally, aggregates are then transferred onto adherent tissue culture dishes in the same media (this time in the absence of DMSO) to allow for subsequent cardiac differentiation (FIG. 9A, adapted from Skerjanc et al. 1999; Trends in Cardiovascular Medicine, volume 9, pages 139-143). The cardiac specific marker Troponin T (cTnT) was used (by immunofluorescence) to identify differentiated cells. Treatment with hCT1 significantly inhibited the differentiation of cardiac cells (at day 7) at any dose used as assessed by the number of cardiac cells per total nuclei (cTnT+/DAPI+) whereby a significant increase was detected only in the non-treated cells (n=3; *, P<0.05) (FIG. 9B).

Figure 9C:
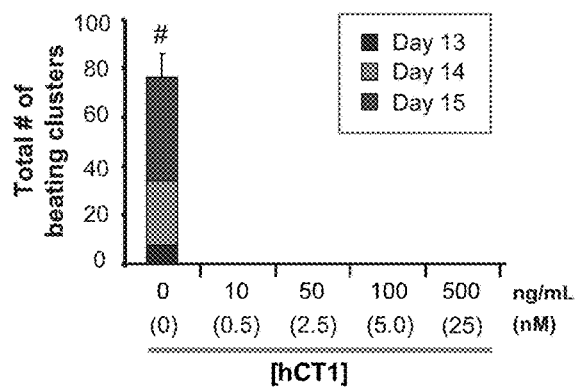
Figure 9D:
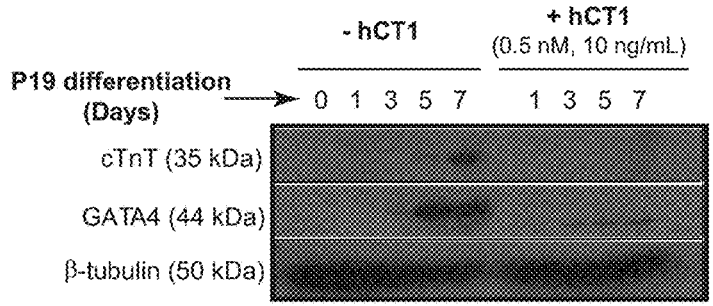

Differentiation was also followed up to day 15 and the number of visually beating clusters was used to assess cardiac differentiation. A significant increase in the number of beating clusters was detected at days 13, 14, and 15 only in the non-treated cells (n=3; #, P<0.05) whereas no beating clusters were detected in the presence of hCT1 (FIG. 9C). Whole cell lysates were also obtained from a P19 cardiac differentiation time course at days 0, 1, 3, 5, and 7 in the presence or absence of 10 ng/mL (0.5 nM) hCT1 and probed for the cardiac-specific markers cTnT and GATA4 by immunoblot. α-tubulin was used as a loading control. By days 5 and 7, GATA4 and cTnT were strongly expressed in the absence of hCT1; respectively. However, hCT1 significantly inhibited GATA4 and cTnT expression. Applicants have thus shown a robust inhibition of cardiac differentiation in mouse P19 cells suggesting that the benefit afforded by CT-1 is primarily due to its role in beneficial remodeling/physiological adaptive compensation and not likely in regenerating new cardiac tissue.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method for treating a patient with right ventricular failure (RVF) due to pressure overload, by inducing right ventricular (RV) adaptive compensation in the patient, comprising administration of a therapeutically effective amount of a cardiotrophin-1 (CT-1) polypeptide of a sequence corresponding to that of a naturally occurring mammalian CT-1 polypeptide to the patient to treat right ventricular failure (RVF).

2. The method according claim 1, wherein the pressure overload is due to pulmonary hypertension (PH).

3. The method according to claim 2, wherein the pressure overload is due to pulmonary arterial hypertension (PAH).

4. The method according to claim 1, wherein the pressure overload is due to heart failure with preserved ejection fraction (HFpEF).

5. The method according to claim 1, wherein to treat RVF is to prevent RVF.

6. The method according to claim 1, wherein to treat RVF is to delay RVF.

7. The method according to claim 1, wherein to treat RVF is to relieve, reduce or alleviate RVF.

8. The method according to claim 1, wherein the CT-1 polypeptide is recombinant human CT-1 polypeptide.

9. The method according to claim 1, wherein the adaptive compensation includes a characteristic selected from among the following: eccentric hypertrophy, an increased RVLW (right ventricle lateral wall) thickness but constant or reduced RVID:LVID (right to left ventricle internal diameters) ratio, an increased vascularity, and maintenance of efficient contractile function or improved contractile function, and combinations thereof.

10. A method for reversing RV maladaptive compensation in a patient with right ventricular failure due to pressure overload, comprising administration of a therapeutically effective amount of a cardiotrophin-1 (CT-1) polypeptide of a sequence corresponding to that of a naturally occurring mammalian CT-1 polypeptide to the patient to treat right ventricular failure (RVF).

* * * * *

UNITED STATES PATENT AND TRADEMARK OFFICE
CERTIFICATE OF CORRECTION

| | |
|---|---|
| PATENT NO. | : 9,962,427 B2 |
| APPLICATION NO. | : 15/206889 |
| DATED | : May 8, 2018 |
| INVENTOR(S) | : Colin Suen et al. |

Page 1 of 1

It is certified that error appears in the above-identified patent and that said Letters Patent is hereby corrected as shown below:

In the Specification

Column 5, Line 49, after '(right)' insert a --.--

Column 9, Line 35, after 'RV' insert a --.--; Line 51, after 'capillaries' insert a --.--

In the Claims

Column 26, Line 13, after 'according' insert --to--

Signed and Sealed this
Eleventh Day of December, 2018

Andrei Iancu
*Director of the United States Patent and Trademark Office*